(12) United States Patent
Gurtner et al.

(10) Patent No.: US 11,701,262 B2
(45) Date of Patent: Jul. 18, 2023

(54) DEVICES AND METHODS FOR SKIN TIGHTENING

(71) Applicant: Neodyne Biosciences, Inc., Newark, CA (US)

(72) Inventors: Geoffrey C. Gurtner, Palo Alto, CA (US); Michael T. Longaker, Atherton, CA (US); Reinhold H. Dauskardt, Menlo Park, CA (US); Paul Yock, Atherton, CA (US); John A. Zepeda, Los Altos, CA (US); Kenneth N. Horne, San Francisco, CA (US); Bankim H. Mehta, San Ramon, CA (US); Michael H. Rosenthal, Menlo Park, CA (US); Joseph Rimsa, Palo Alto, CA (US); Sergio Salinas, Redwood City, CA (US); Melanie Harris, Santa Ana, CA (US); Greg Spooner, San Francisco, CA (US); Kin Chan, Menlo Park, CA (US)

(73) Assignee: Neodyne Biosciences, Inc., Newark, CA (US)

( * ) Notice: Subject to any disclaimer, the term of this patent is extended or adjusted under 35 U.S.C. 154(b) by 488 days.

(21) Appl. No.: 16/026,895

(22) Filed: Jul. 3, 2018

(65) Prior Publication Data
US 2019/0015255 A1    Jan. 17, 2019

Related U.S. Application Data

(63) Continuation of application No. 13/411,443, filed on Mar. 2, 2012, now abandoned.
(Continued)

(51) Int. Cl.
*A61F 13/00* (2006.01)
*A61F 13/02* (2006.01)
(Continued)

(52) U.S. Cl.
CPC ...... *A61F 13/00038* (2013.01); *A61B 18/203* (2013.01); *A61F 13/00* (2013.01);
(Continued)

(58) Field of Classification Search
CPC .... A61F 13/00; A61F 13/00038; A61F 13/02; A61F 2013/00374; A61F 2013/006;
(Continued)

(56) References Cited

U.S. PATENT DOCUMENTS

| 114,750 A | 5/1871 | Battersby |
| 363,538 A | 5/1887 | Penny |

(Continued)

FOREIGN PATENT DOCUMENTS

| AU | 2010282523 A1 | 4/2012 |
| CA | 2321491 A1 | 9/1999 |

(Continued)

OTHER PUBLICATIONS

English translation of Decision for Patent Grant for KR Application No. 10-2013-7026319, dated Oct. 14, 2019.
(Continued)

*Primary Examiner* — Caitlin A Carreiro
(74) *Attorney, Agent, or Firm* — Dorsey & Whitney LLP

(57) ABSTRACT

The methods, procedures, kits, and devices described herein assist with the healing process of tissue that was previously or simultaneously treated for a therapeutic or cosmetic effect. The methods, procedures, kits, and devices described herein can also provide temporary simulated results of a cosmetic procedure to allow for visual assessment to select the type of procedure or for treatment planning in advance of the surgical procedure.

12 Claims, 29 Drawing Sheets

Related U.S. Application Data

(60) Provisional application No. 61/605,717, filed on Mar. 1, 2012, provisional application No. 61/476,163, filed on Apr. 15, 2011, provisional application No. 61/448,809, filed on Mar. 3, 2011.

(51) Int. Cl.
    *A61B 18/20* (2006.01)
    *A61B 17/00* (2006.01)
    *A61B 18/00* (2006.01)

(52) U.S. Cl.
    CPC ...... *A61F 13/00029* (2013.01); *A61F 13/023* (2013.01); *A61F 13/0223* (2013.01); *A61F 13/0226* (2013.01); *A61F 13/0256* (2013.01); *A61F 13/0259* (2013.01); *A61B 2017/00765* (2013.01); *A61B 2018/0047* (2013.01); *A61F 2013/006* (2013.01); *A61F 2013/00374* (2013.01)

(58) Field of Classification Search
    CPC ............ A61F 13/00029; A61F 13/0223; A61F 13/0226; A61F 13/023; A61F 13/0256; A61F 13/0259; A61F 13/00021; A61F 2013/53925; A61B 18/203; A61B 2017/00765; A61B 2018/0047; A61B 17/08; A61N 2005/067
    USPC ............ 602/41, 52, 53, 54, 74, 55; 604/308; 606/215, 218; 607/2, 1, 89
    See application file for complete search history.

(56) References Cited

U.S. PATENT DOCUMENTS

| | | |
|---|---|---|
| 633,050 A | 9/1899 | Spenard |
| 1,074,413 A | 9/1913 | Baun et al. |
| 1,774,489 A | 8/1930 | David |
| 1,969,188 A | 8/1934 | Spicer |
| 2,018,517 A | 10/1935 | Edward |
| 2,303,131 A | 11/1942 | Morgan |
| 2,371,978 A | 3/1945 | Perham |
| 2,421,193 A | 5/1947 | James |
| 2,472,009 A | 5/1949 | James |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-sierra et al. |
| 4,073,298 A | 2/1978 | Le |
| 4,114,624 A | 9/1978 | Haverstock |
| 4,141,363 A | 2/1979 | James et al. |
| 4,173,131 A | 11/1979 | Melton et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | Mccracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schaefer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | Mclorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,472,581 B1 | 10/2002 | Muramatsu et al. |
| 6,485,503 B2 | 11/2002 | Jacobs et al. |
| 6,495,230 B1 | 12/2002 | Do |

(56) References Cited

U.S. PATENT DOCUMENTS

| | | |
|---|---|---|
| 6,570,051 B1 | 5/2003 | Beaudry |
| 6,572,878 B1 | 6/2003 | Blaine |
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,100,615 B1 * | 9/2006 | Kert .............. A61N 5/0616 606/9 |
| 7,122,712 B2 | 10/2006 | Lutri et al. |
| 7,135,606 B1 | 11/2006 | Dozier et al. |
| 7,227,050 B2 | 6/2007 | Sigurjonsson et al. |
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |
| 7,511,185 B2 | 3/2009 | Lebner |
| 7,563,941 B2 | 7/2009 | Lebner et al. |
| 7,683,234 B2 | 3/2010 | Gurtner et al. |
| 7,834,232 B2 | 11/2010 | Rastegar et al. |
| RE42,126 E | 2/2011 | Ye et al. |
| 8,063,263 B2 | 11/2011 | Gurtner et al. |
| 8,168,850 B2 | 5/2012 | Gurtner et al. |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 | 11/2013 | Zepeda et al. |
| 8,674,164 B2 | 3/2014 | Zepeda et al. |
| 9,248,048 B2 | 2/2016 | Jackson et al. |
| 9,248,051 B2 | 2/2016 | Gurtner et al. |
| 9,358,099 B2 | 6/2016 | Naor et al. |
| 9,492,329 B2 | 11/2016 | Zepeda et al. |
| 2002/0013300 A1 | 1/2002 | Capelli-schellpfeffer |
| 2002/0193723 A1 | 12/2002 | Girardin et al. |
| 2003/0014053 A1 | 1/2003 | Nguyen et al. |
| 2003/0040687 A1 | 2/2003 | Boynton et al. |
| 2003/0092969 A1 | 5/2003 | Omalley et al. |
| 2003/0220700 A1 | 11/2003 | Hammer et al. |
| 2005/0033215 A1 | 2/2005 | Lebner |
| 2005/0034731 A1 | 2/2005 | Rousseau et al. |
| 2005/0070956 A1 | 3/2005 | Rousseau |
| 2005/0080453 A1 | 4/2005 | Lebner et al. |
| 2005/0095275 A1 | 5/2005 | Zhu et al. |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2005/0283141 A1 | 12/2005 | Giovannoli |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0246802 A1 | 11/2006 | Hughes et al. |
| 2006/0282135 A1 | 12/2006 | Tankovich |
| 2007/0032845 A1 * | 2/2007 | Neuberger .............. A61N 5/062 607/89 |
| 2007/0093161 A1 | 4/2007 | Eede et al. |
| 2007/0129776 A1 | 6/2007 | Robins et al. |
| 2007/0142761 A1 | 6/2007 | Aali |
| 2007/0191752 A1 | 8/2007 | Lebner |
| 2007/0239232 A1 | 10/2007 | Kurtz et al. |
| 2007/0239236 A1 * | 10/2007 | Manstein .............. A61B 18/203 607/89 |
| 2007/0282235 A1 | 12/2007 | Beaudry |
| 2007/0282374 A1 | 12/2007 | Sogard et al. |
| 2008/0033334 A1 * | 2/2008 | Gurtner ................ C07K 5/0806 602/53 |
| 2008/0051687 A1 | 2/2008 | Rogers |
| 2008/0172047 A1 * | 7/2008 | Altshuler .............. A61H 39/002 606/9 |
| 2008/0208098 A1 | 8/2008 | Rennix |
| 2008/0228220 A1 | 9/2008 | Weiser |
| 2008/0269658 A1 * | 10/2008 | Vinton ................ A61M 35/00 602/59 |
| 2009/0131845 A1 | 5/2009 | Gurtner et al. |
| 2009/0131846 A1 | 5/2009 | Gurtner et al. |
| 2009/0163844 A1 | 6/2009 | Gurtner et al. |
| 2009/0177136 A1 | 7/2009 | Liedtke et al. |
| 2010/0191253 A1 | 7/2010 | Oostman, Jr. et al. |
| 2010/0280428 A1 | 11/2010 | Widgerow et al. |
| 2011/0152738 A1 | 6/2011 | Zepeda et al. |
| 2011/0319798 A1 | 12/2011 | Digrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0083724 A1 | 4/2012 | Zepeda et al. |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0184629 A1 | 7/2013 | Gurtner et al. |
| 2013/0190673 A1 | 7/2013 | Gurtner et al. |
| 2013/0281904 A1 | 10/2013 | Jackson et al. |
| 2014/0088481 A1 | 3/2014 | Jackson et al. |
| 2014/0135677 A1 | 5/2014 | Zepeda et al. |
| 2014/0135678 A1 | 5/2014 | Zepeda et al. |
| 2016/0213522 A1 | 7/2016 | Gurtner et al. |
| 2017/0020522 A1 | 1/2017 | Yock |

FOREIGN PATENT DOCUMENTS

| | | | |
|---|---|---|---|
| CA | 2621387 A1 | 3/2007 | |
| CA | 2659772 A1 | 2/2008 | |
| CN | 1414842 A | 4/2003 | |
| CN | 1608604 A | 4/2005 | |
| CN | 101563113 A | 10/2009 | |
| CN | 201481501 U | 5/2010 | |
| CN | 102665623 A | 9/2012 | |
| EP | 2161011 A1 | 3/2010 | |
| EP | 2464322 A2 | 6/2012 | |
| GB | 2424584 A * | 10/2006 | .......... A61J 15/0026 |
| JP | 2004515256 A | 5/2004 | |
| JP | 2004223087 A | 8/2004 | |
| JP | 2004536898 A | 12/2004 | |
| JP | 2006513748 A | 4/2006 | |
| JP | 2007531578 A | 11/2007 | |
| JP | 2007537781 A | 12/2007 | |
| JP | 2009545382 A | 12/2009 | |
| JP | 2013501591 A | 1/2013 | |
| KR | 20080007084 A | 1/2008 | |
| KR | 20100094700 A | 8/2010 | |
| KR | 20100129958 A | 12/2010 | |
| KR | 20140020993 A | 2/2014 | |
| RU | 2019138 C1 | 9/1994 | |
| WO | 1997017919 A1 | 5/1997 | |
| WO | 1997030700 A2 | 8/1997 | |
| WO | 1997030700 A3 | 8/1997 | |
| WO | 2000053139 A1 | 9/2000 | |
| WO | 2001039693 A2 | 6/2001 | |
| WO | 2002015816 A2 | 2/2002 | |
| WO | 2002015816 A3 | 2/2002 | |
| WO | 2002045698 A2 | 6/2002 | |
| WO | 2002045698 A3 | 6/2002 | |
| WO | 2002087645 A1 | 11/2002 | |
| WO | 2002092783 A2 | 11/2002 | |
| WO | 2002092783 A3 | 11/2002 | |
| WO | 2004060413 A1 | 7/2004 | |
| WO | 2004073567 A1 | 9/2004 | |
| WO | 2005079674 A1 | 9/2005 | |
| WO | 2005096979 A1 | 10/2005 | |
| WO | 2005096981 A2 | 10/2005 | |
| WO | 2005096981 A3 | 3/2006 | |
| WO | 2006124671 A2 | 11/2006 | |
| WO | 2006124671 A3 | 4/2007 | |
| WO | 2008019051 A2 | 2/2008 | |
| WO | 2008019051 A3 | 4/2008 | |
| WO | 2011019859 A2 | 2/2011 | |

(56) References Cited

FOREIGN PATENT DOCUMENTS

| WO | 2011019859 A3 | 4/2011 |
|---|---|---|
| WO | 2012094648 A1 | 7/2012 |
| WO | 2012119131 A1 | 9/2012 |

OTHER PUBLICATIONS

English translation of Decision to Grant a Patent for JP Application No. 2017-192700, dated May 8, 2020.
English translation of KR Office Action for Application No. 10-2020-7001161, dated Mar. 18, 2020.
English translation of Notice of Final Rejection for JP Application No. 2017-192700, dated Nov. 19, 2019.
English translation of BR Office Action for Application No. 1120130225254, dated Sep. 18, 2019.
English translation of CN Office Action for Application No. 201810545618.4, dated Jul. 3, 2020.
English Translation of Decision to Grant received in KR App. No 10-2020-7001161 dated Sep. 4, 2020.
"NHSSB Wound Management Manual", Northern Health and Social Services Board, 2005, pp. 1-97.
3M Healthcare, "3M™ Steri-Strip™ Adhesive Skin Closures (Reinforced): Commonly Asked Questions", 3M Healthcare, St. Paul, MN, Jun. 27, 2002, pp. 1-4.
3M Healthcare, "3M™ Steri-Strip™ S Surgical Skin Closure Application Examples, Comparisons, and Results", 3M Healthcare St. Paul, MN, 2007, 4 pages.
3M Healthcare, "3M™ Steri-Strip™ S Surgical Skin Closure Patient Care Information", 3M Healthcare, St. Paul, MN, 2006, 2 pages.
3M Healthcare, "3M™ Steri-Strip™ S Surgical Skin Closure The Simple, Non-Invasive Alternative to Staples and Sutures from the Steri-Strip Family", 3M Healthcare, St. Paul, MN, 2006, 2 pages.
3M Healthcare, "3M™ Steri-Strip™ S Surgical Skin Closure", 3M Healthcare, St. Paul, MN, 1 page.
3M Healthcare, "3M™ Steri-Strip™ S Surgical Skin Closure. Application Instructions", 3M Healthcare, 2007, 2 pages.
3M Healthcare, "3M™ Steri-Strip™ S Surgical Skin Closure Commonly Asked Questions", 3M Healthcare, St. Paul, MN, Oct. 19, 2006, pp. 1-8.
3M Healthcare, "3M™ Steri-Strip™ Surgical Skin Closure Poster of Available Sizes", 3M Healthcare, St. Paul, MN, 3 pages.
3M Healthcare, "Reducing the Risk of Superficial Skin Damage Related to Adhesive Use", 3M Healthcare, St. Paul, MN, 2001, 2 pages.
3M Healthcare, "Steri-Strip: Skin Closures", Product Insert, 3M Healthcare, St. Paul, MN 2003, 1 page.
3M Healthcare, "They Say Every Scar Tells a Story", 3M Healthcare, St. Paul, MN, 2006, 1 page.
3M Healthcare, "Tips for Trouble-Free Taping", 3M Healthcare, St. Paul, MN, May 2004, 4 pages.
3M Healthcare, 3M™ Steri-Strip™ S Surgical Skin Closure Application Instructions, 3M Healthcare, St. Paul, MN, 2007, 2 pages.
Anonymous, "3M™ Steri-Strip™ Adhesive Skin Closures", 3M Brochure, 2003, 12 pages.
Anonymous, "3M™ Tegaderm™ Family of Transparent Dressings", 3M Brochure, 2005, 6 pages.
Anonymous, "Avocet Polymet Technologies, Inc.", available online at <http:/www.avocetcorp.com/index.html>, last visited on Nov. 5, 2007, 2 pages.
Anonymous, "Avogel Scar Hydrogel,", available online at <http://avocetcorp.com/avogel_scar_hydrogel.html>, last visited on Nov. 5, 2007, 1 page.
Anonymous, "Avosil Ointment", available online at <http://www.avocetcorp.com/avosil.html>, last visited on Nov. 5, 2007, 3 pages.
Anonymous, "Mepiform Instructions of Use", Tendra Corporation Brochure, 2 pages.
Anonymous, "Silicone Scar Bandage: Standard Wound Healing Application", available online at <http://www.thejamushop.com/silicon_sheet_for_keloids.htm>, last visited on Mar. 18, 2009, 4 pages.
Brace, "Definition of Brace", Merriam Webster, Available Online at <www.merriam-webster.com>, 2015, 4 pages.
Canica Design Inc., "ABRA Abdominal Wall Closure Set: A Dynamic Wound Closure System", Instructions for Use, available online at <http://www.canica.com/instructions/1D1544%20ABRA%20CWK08.pdf>, last visited on Sep. 10, 2009, pp. 1-11.
Canica Design Inc., "ABRA Surgical Skin Closure Set: A Dynamic Wound Closure System", available online at <http://www.canica.com/instructions/1D0830.pdf>, last visited on Sep. 10, 2009, pp. 1-4.
Decision for Grant received for Korean Patent Application No. 10-2009-7003220, dated May 14, 2014, 3 pages.
Decision for Grant received for Korean Patent Application No. 10-2014-7005383, dated Dec. 10, 2014, 3 pages.
Decision of Grant Received for Chinese Patent Application No. 201280012003.6, dated Feb. 3, 2015, 2 pages.
English Translation of Notice Grounds for Preliminary Rejection dated Feb. 8, 2019 for Korean application No. 10-2013-7026319.
English Translation of First Office Action dated Apr. 2, 2019 for Japanese application No. 2017-192700.
Extended European Search Report (includes Supplementary European Search Report and Search Opinion) received for European Patent Application No. 12752239.9, dated Oct. 1, 2014, 7 pages.
Extended European Search Report and European Search Opinion received for European Patent Application No. 10808724.8, dated Aug. 19, 2013, 8 pages.
International Preliminary Report on Patentability received for PCT Application No. PCT/US2013/025449, dated Feb. 5, 2015, 7 pages.
International Preliminary Report on Patentability received for PCT Patent Application No. PCT/US2007/017320, dated Feb. 3, 2009, 8 pages.
International Preliminary Report on Patentability received for PCT Patent Application No. PCT/US2010/045239, dated Feb. 23, 2012, 10 pages.
International Preliminary Report on Patentability received for PCT Patent Application No. PCT/US2012/020561, dated Jul. 18, 2013, 8 pages.
International Preliminary Report on Patentability received for PCT Patent Application No. PCT/US2012/025510, dated Aug. 29, 2013, 10 pages.
International Preliminary Report on Patentability received for PCT Patent Application No. PCT/US2012/027618, dated Sep. 12, 2013, 12 pages.
International Search Report and Written Opinion received for PCT Patent Application No. PCT/US2007/017320, dated Feb. 7, 2008, 10 pages.
International Search Report and Written Opinion Received for PCT Patent Application No. PCT/US2010/045239, dated Feb. 8, 2011, 12 pages.
International Search Report and Written Opinion received for PCT Patent Application No. PCT/US2012/020561, dated May 1, 2012, 9 pages.
International Search Report and Written Opinion received for PCT Patent Application No. PCT/US2012/025510, dated May 29, 2012, 11 pages.
International Search Report and Written Opinion received for PCT Patent Application No. PCT/US2012/027618, dated Jun. 28, 2012, 11 pages.
International Search Report and Written Opinion received for PCT Patent Application No. PCT/US2013/25449, dated Apr. 23, 2013, 7 pages.
Mask, "Definition of Mask", Merriam Webster, Available Online at <www.merriam-webster.com>, 2015, 4 pages.
Notice of Acceptance Received for Australian Patent Application No. 2010282523, dated Jul. 2, 2015, 2 pages.
Notice of Allowance received for Israel Patent Application No. 218020, dated Dec. 11, 2014, 4 pages.
Notice of Allowance received for Japanese Patent Application No. 2009-522879, dated Mar. 17, 2014, 6 pages.
Notice of Allowance received for Japanese Patent Application No. 2012-524855, dated Apr. 30, 2015, 3 pages.
Notice of Allowance received for Japanese Patent Application No. 2013-037053, dated Jan. 6, 2015, 3 pages.

(56) References Cited

OTHER PUBLICATIONS

Office Action received for Australian Patent Application No. 2010282523, dated May 6, 2014.
Office Action received for Australian Patent Application No. 2012204174, dated Aug. 4, 2015, 2 pages.
Office Action received for Canadian Patent Application No. 2,659,772, dated Oct. 30, 2013, 3 pages.
Office Action received for Canadian Patent Application No. 2,659,772, dated Sep. 11, 2014, 2 pages.
Office Action received for Chinese Patent Application No. 201080045471.4, dated Sep. 29, 2013, 4 pages.
Office Action received for Chinese Patent Application No. 201080045471.4, dated May 21, 2014, 6 pages.
Office Action received for Chinese Patent Application No. 2012280021431.5 dated Jul. 17, 2015, 4 pages.
Office Action received for Chinese Patent Application No. 201280012003.6, dated Jun. 30, 2014, 9 pages.
Office Action received for Chinese Patent Application No. 201280021431.5, dated Sep. 22, 2014, 3 pages.
Office Action received for Chinese Patent Application No. 201310474149.9, dated Jan. 27, 2015, 10 pages.
Office Action received for Chinese Patent Application No. 201310474149.9, dated Jul. 27, 2015, 6 pages.
Office Action received for European Patent Application No. 07836471.8, dated Jul. 13, 2010, 7 pages.
Office Action received for European Patent Application No. 10808724.8, dated Jan. 15, 2015, 4 pages.
Office Action received for Indian Patent Application No. 654/DELNP/2009, dated Jul. 31, 2014, 4 pages.
Office Action received for Israeli Patent Application No. 218020, dated Dec. 1, 2013, 12 pages.
Office Action Received for Japanese Patent Application No. 2012-524855, dated Apr. 14, 2014, 7 pages.
Office Action received for Japanese Patent Application No. 2012-524855, dated Oct. 24, 2014, 5 pages.
Office Action received for Japanese Patent Application No. 2013-037053, dated Mar. 17, 2014, 5 pages.
Office Action received for Japanese Patent Application No. 2013548594, dated Jul. 7, 2015, 10 pages.
Office Action Received for Japanese Patent Application No. 2014-123100, dated May 18, 2015, 1 page.
Office Action received for Japanese Patent Application No. 2014-143959, dated May 1, 2015, 2 pages.
Office Action received for Korean Patent Application No. 10-2009-7003220, dated Oct. 28, 2013, 6 pages.
Office Action Received for Korean Patent Application No. 10-2014-7005383, dated May 14, 2014, 6 pages.
Shanghai Dongyue Medical Health Product Co., Ltd., "Silicon-gel Membrane-Scar Bandage", available online at <http://shdongyue.com/cp/shaos/shaos02b.asp>, last visited on Nov. 6, 2008, 2 pages.
Smith & Newphew, "CICA-CARE* Silicone Gel Sheeting", available online at <http://wound.smith-nephew.com/za/Product.asp?NodeId=569&Tab=5&Hide=True>, last visited on Jun. 9, 2009, 1 page.
Wound Care Technologies, "DERMAClose™ RC: Continuous External Tissue Expander", available online at <http://www.woundcaretech.com/sell-sheet.pdf>, last visited on Sep. 10, 2009, 2008, 2 pages.
Wound Care Technologies, "Instructions for Use. DERMAClose™ RC", available online at <http://www.dermaclose.com/instructions.pdf>, last visited on Sep. 10, 2009, 2008, 2 pages.
Extended European Search Report (includes Supplementary European Search Report and Search Opinion); European Patent Application No. 12732236.0, dated Jun. 29, 2015., pp. all.
Intention to Grant; European Patent Application No. 12752239.9, dated Sep. 24, 2015., pp. all.
Aarabi et al., "Mechanical Load Initiates Hypertrophic Scar Formation Through Decreased Cellular Apoptosis", The FASEB Journal, vol. 21, Oct. 2007, pp. 3250-3261.
Al-Attar et al., "Keloid Pathogenesis and Treatment", Plastic and Reconstructive Surgery, vol. 117, No. 1, Jan. 2006, pp. 286-300.

Angelini et al., "Comparative Study of Leg Wound Skin Closure in Coronary Artery Bypass Graft Operations", Thorax, vol. 39, 1984, pp. 942-945.
Atkinson, et al., "A Randomized, Controlled Trial to Determine the Efficacy of Paper Tape in Preventing Hypertrophic Scar Formation in Surgical Incisions that Traverse Langer's Skin Tension Lines", Plastic and Reconstructive Surgery, vol. 116, No. 6, Nov. 2005., pp. 1648-1656.
Bachert et al., "Probing Elastic Modulus and Depth of a Two Layer Human Skin Model with Piezoelectric Cantilevers", Biomedical Engineering Senior Design Team, Drexel University, 2003, pp. 1-27.
Berman et al., "Keloid and Hypertrophic Scar", available online at <http://www.emedicine.com/DERM/topic205.htm>, last visited on Nov. 19, 2007, 23 pages.
Bunker, Timothy D., "Problems with the Use of Op-Site Sutureless Skin Closures in Orthopaedic Procedures", Annals of the Royal College of Surgeons of England, vol. 65, 1983, pp. 260-262.
Burd et al., "Hypertrophic Response and Keloid Diathesis: Two Very Different Forms of Scar", Plastic and Reconstructive Surgery, vol. 116, No. 7, Dec. 2005, pp. 150e-157e.
Chen et al., "Prospective Study Comparing Wounds Closed with Tape with Sutured Wounds in Colorectal Surgery,", Arch. Surg., vol. 136, Jul. 2001, pp. 801-803.
Davison et al. "Ineffective Treatment of Keloids with Interferon Alpha-2b", Plastic and Reconstructive Surgery, vol. 117, No. 1, Jan. 2006, pp. 247-252.
Escoffier et al., "Age-Related Mechanical Properties of Human Skin: An in Vivo Study", The Journal of Investigate Dermatology, vol. 93, No. 3, Sep. 1989, pp. 353-357.
Evans et al., "Measuring the Mechanical Properties of Human Skin in vivo Using Digital Image Correlation and Finite Element Modelling", J. Strain Analysis, vol. 44, 2009, pp. 337-345.
Fairclough et al., "The Use of Sterile Adhesive Tape in the Closure of Arthroscopic Puncture Wounds: A Comparison with a Single Layer Nylon Closu", Annals of the Royal College of Surgeons of England, vol. 69, 1987, pp. 140-141.
Gorney, Mark, "Scar: The Trigger to the Claim", The American Society of Plastic Surgeons, vol. 117, No. 3, 2006, pp. 1036-1037.
Hof et al., "Comparing Silicone Pressure-Sensitive Adhesives to Silicone Gels for Transdermal Drug Delivery", Presented at 33 Annual Meeting and Exposition to the Controlled Release Society, Vienna, Austria, Jul. 22-26, 2006, 7 pages.
Koval et al., "Tape Blisters Following Hip Surgery, A Prospective Randomized Study of Two Types of Tape", The Journal of Bone and Joint Surgery, vol. 85-A, No. 10, Oct. 2003, pp. 1884-1887.
Kuo et al., "Prospective, Randomized, Blinded Study of a New Wound Closure Film Versus Cutaneous Suture for Surgical Wound Closure", Dermatologic Surgery, vol. 32, No. 5, May 2006, pp. 676-681.
Mustoe et al., "A Randomized, Controlled Trial to Determine the Efficacy of Paper Tape in Preventing Hypertrophic Scar Formation in Surgical Incisions that Traverse Langer's Skin Tension Lines", Plastic and Reconstructive Surgery, Nov. 2005., pp. 1657-1658.
Nahabedian, Maurice Y., "Scar Wars: Optimizing Outcomes with Reduction Mammaplasty", Plastic and Reconstructive Surgery, vol. 116, No. 7, Dec. 2005, pp. 2026-2029.
O'Brien et al., "Silicon Gel Sheeting for Preventing and Treating Hypertrophic and Keloid Scars (Review)", The Cochrane Collaboration, 2009, pp. 1-47.
Pitcher, David, "Sutureless Skin Closure for Pacemaker Implantation: Comparison with Subcuticular Suture", Postgraduate Medical Journal, vol. 59, Feb. 1983, pp. 83-85.
Shirado et al., "Realization of Human Skin-Like Texture by Emulating Surface Shape Pattern and Elastic Structure", Presented at Symposium on Haptic Interfaces for Virtual Environment and Teleoperator Systems, Mar. 25-26, 2006, Alexandria, VA, pp. 295-296.
Sullivan et al., "Acute Wound Care", Chapter 7 in ACS Surgery: Principles and Practice, 2007, pp. 1-24.
Teot, Luc, "Scar Evaluation and Management: Recommendations", European Tissue Repair Society, Scar Control I. ETRS—Bulletin

(56) References Cited

OTHER PUBLICATIONS 12.1 & 2, available online at <http://www.etrs.org/bulletin12_1/section11.php>, last visisted on Nov. 30, 2007, 13 pages.
Vaughan et al., "Optimal Closure of Surgical Wounds in Forefoot Surgery: Are Adhesive Strips Beneficial?", Acta Orthop. Belg., vol. 72, No. 6, 2006, pp. 731-733.
Vowden, Kathryn, "Wound Management, Policy and Resource Pack", Bradford Teaching Hospitals NHS Foundation Trust, Mar. 2003, pp. 1-72.
Watson et al., "Op-Site Skin Closure: A Comparison with Subcuticular and Interrupted Sutures,", Annals of the Royal College of Surgeons of England, vol. 65, 1983, pp. 83-84.
Webster et al., "Closure of Abdominal Wounds by Adhesive Strips: A Clinical Trial,", British Medical Journal, vol. 20, Sep. 20, 1975, pp. 696-697.
Westaby, S., "Evaluation of a New Product for Sutureless Skin Closure", Annals of the Royal College of Surgeons of England, vol. 62, 1980, pp. 129-132.

\* cited by examiner

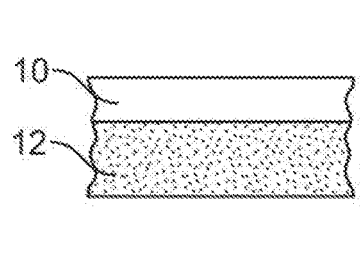
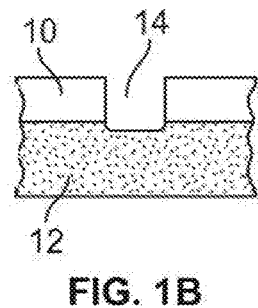
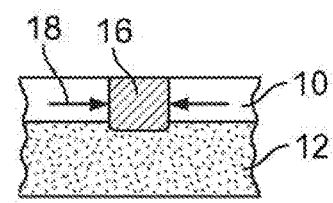
FIG. 1A  FIG. 1B  FIG. 1C
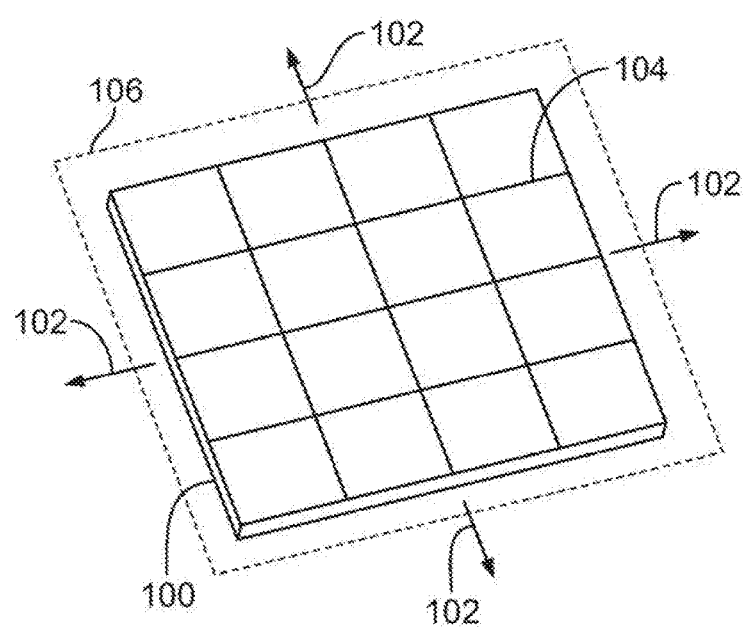
FIG. 2A
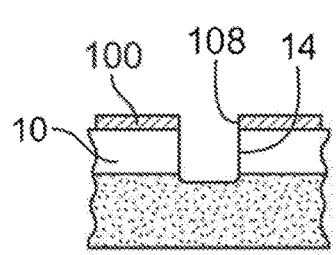
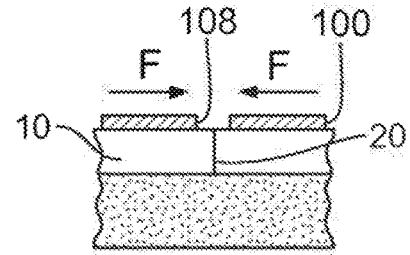
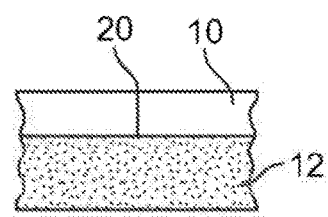
FIG. 2B  FIG. 2C  FIG. 2D

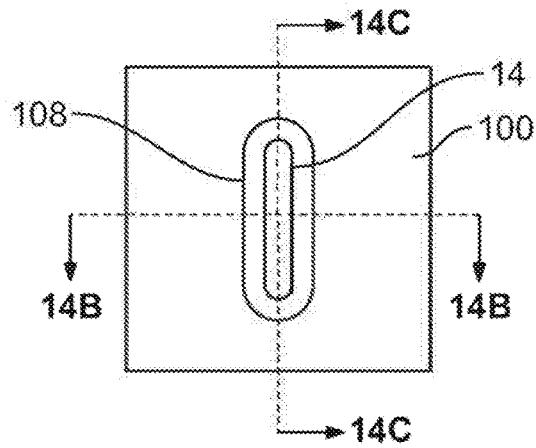
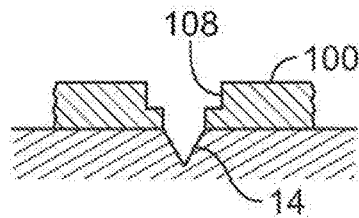
FIG. 14A
FIG. 14B
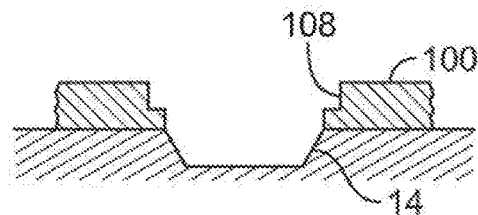
FIG. 14C
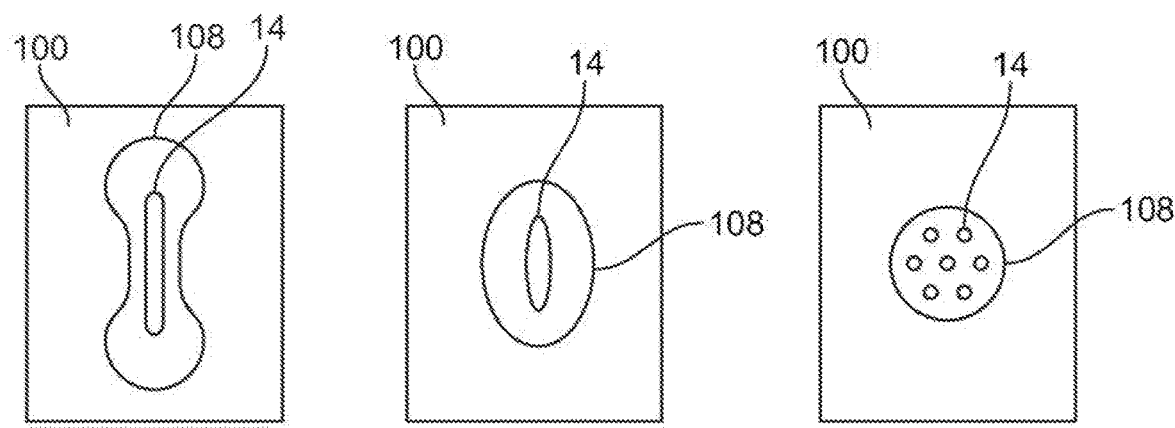
FIG. 14D

DEVICES AND METHODS FOR SKIN TIGHTENING

CROSS-REFERENCE TO RELATED APPLICATIONS

This application is a continuation of U.S. application Ser. No. 13/411,443, filed on Mar. 2, 2012, which claims benefit under 35 U.S.C. § 119(e) to a) U.S. Provisional Application Ser. No. 61/448,809, filed on Mar. 3, 2011, b) U.S. Provisional Application Ser. No. 61/476,163, filed on Apr. 15, 2011, and c) U.S. Provisional Application Ser. No. 61/605,717, filed on Mar. 1, 2012, all of which are hereby incorporated by reference in their entirety. This application is also related to U.S. application Ser. No. 11/888,978, filed on Aug. 3, 2007, U.S. application Ser. No. 12/854,859, filed on Aug. 11, 2010, and U.S. application Ser. No. 13/345,524, filed Jan. 6, 2012, all of which are hereby incorporated by reference in their entirety.

FIELD OF THE INVENTION

The present invention relates generally to medical devices, kits and methods used for improved healing of skin after a therapeutic injury. For example, such devices, kits and methods can be used to produce improved tightening of skin after a therapeutic treatment. The devices, kits and methods can also be used to produce a temporary cosmetic effect by displacing skin to stimulate a clinical effect.

BACKGROUND OF THE INVENTION

Many procedures involve producing a therapeutic injury to tissue to produce an improved therapeutic or cosmetic effect in the tissue. Skin tightening is one such therapy that involves creating an injury to produce an improved cosmetic appearance of the skin near or around the site of the therapeutic injury. Skin tightening can be performed many different ways ranging from invasive treatments to less invasive procedures such as IPL (intense pulsed light). Typically invasive procedures appear to be the most effective but require significant recuperative periods, while less invasive procedures are less effective than invasive procedures but the recuperative periods are shorter. In any case, the healing process that occurs subsequent to the therapeutic injury can determine the effectiveness of the procedure.

Again, in referring to skin tightening as one example, during the procedure a physician or medical practitioner induces a controlled trauma in the skin. This is typically performed by applying energy to the tissue to either ablate (vaporize) or non-ablatively heat the skin to create either patterns of lesions or a localized area of treatment. There are limits when creating therapeutic injury to tissue, if there is variability in the lesion or hole created in the tissue the healing process may not produce the optimal effect. For example, if the therapeutic treatment creates openings in the tissue that are too large, the tissue may not heal as desired.

In one variation, a skin treatment system is provided, comprising an dressing with a load per millimeter width of at least 0.1 Newtons at a strain of at least 0.01, 0.05, 0.1, 0.2, 0.3, 0.4, 0.5, 0.6, 0.7, 0.8, 0.9 or higher, and a limiting member coupled to the dressing and configured to resist straining of the dressing beyond a predetermined strain. The limiting member may comprise a first handle at a first end of the at least one limiting member, and a second handle at a second end of the at least one limiting member. The skin treatment system may comprise at least two elongate strain limiting structures. The first handle may be contiguously or non-contiguously coupled to the dressing between the first ends of the at least two elongate strain limiting structures. The second handle may also be contiguously or non-contiguously coupled to the dressing between the second ends of the at least two elongate strain limiting structures. The predetermined strain may be at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9 or higher. The limiting member may be releasably coupled to the dressing. The limiting member may be adhered to the dressing using an adhesive. The adhesive may comprise a shear-resistance to a force level that is greater than the T-peel resistance to the force level. The first handle and the second handle may comprise a substantially inelastic material relative to the dressing, which may optionally be a semi-rigid or rigid material. The limiting member may comprise at least one flexible, inelastic elongate element. The dressing may comprise an unstrained configuration in which a distance between a first attachment region of the limiting member and a second attachment region of the limiting member is less than a length of the limiting member between the first attachment region and the second attachment region, and may comprise a strained configuration at the predetermined strain wherein the distance between the first attachment region of the limiting member and a second attachment region of the limiting member is substantially equal to the a length of the limiting member between the first attachment region and the second attachment region. The limiting member may comprise a folded board with at least three two folds, or a ratchet and pawl mechanism. The limiting member may be selectively configured to resist straining of the dressing beyond a plurality of predetermined strains. The plurality of predetermined strains may comprise graphical indicia on the limiting member.

In another variation, the skin treatment system comprises an dressing, comprising a tensioning axis, and a limiting member coupled to the dressing and configured to resist straining of the dressing beyond a predetermined strain, wherein the attachment of a first end of the limiting member to the dressing is contiguous across a dimension of the dressing transverse to the tensioning axis. The dressing may have a load per millimeter width of at least 0.1 Newtons at a strain of at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or higher. The limiting member may comprise a first handle at a first end of the at least one limiting member, and a second handle at a second end of the at least one limiting member. The skin treatment system may comprise at least two elongate strain limiting structures. The first handle may be contiguously coupled to the dressing between the first ends of the at least two elongate strain limiting structures. The second handle may also be contiguously coupled to the dressing between the second ends of the at least two elongate strain limiting structures. The predetermined strain may be at least 0.01, 0.05, 0.1, 0.2, 0.3, 0.4, 0.5, 0.6, 0.7, 0.8, 0.9, or higher. The limiting member may be releasably coupled to the dressing. The limiting member may be adhered to the dressing using an adhesive. The adhesive may comprise a shear-resistance to a force level that is greater than the T-peel resistance to the force level. The first handle and the second handle may comprise a substantially inelastic material relative to the dressing, which may optionally be a semi-rigid or rigid material. The limiting member may comprise at least one flexible, inelastic elongate element. The dressing may comprise an unstrained configuration in which a distance between a first attachment region of the limiting member and a second attachment region of the limiting member is less than a length of the limiting member between the first attachment region and the second attachment region, and may comprise a strained configuration at the predetermined strain wherein the distance between the first attachment region of the limiting member and a second attachment region of the limiting member is substantially equal to the a length of the limiting member between the first attachment region and the second attachment region. The limiting member may comprise a folded board with at least three two folds, or a ratchet and pawl mechanism. The limiting member may be selectively configured to resist straining of the dressing beyond a plurality of predetermined strains. The plurality of predetermined strains may comprise graphical indicia on the limiting member.

In another variation, a skin treatment system is provided, comprising an elastic structure, first and second handles attached to opposite regions of the elastic structure, wherein the first and second handles are coupled to the elastic structure and configured to provide a substantially uniform tensile force across the elastic structure; and a strain indicator. The strain indicator may comprises graphical or numerical indicia of the degree of strain.

In one variation, a skin treatment device is provided, comprising a first layer comprising an elastic material pre-stretched to a predetermined strain level and a second layer coupled to the first layer and comprising a brace configured to maintain the first layer at the predetermined strain level while the device is attached to a skin layer of a subject; and comprising at least one second layer opening positionable for treatment of skin therethrough, and a securing element configured to secure the device to skin of a subject during treatment through said at least one second layer opening. The first layer may comprise at least one elastic material opening through the elastic material configured to be aligned with the at least one opening of the second layer for treatment through the aligned openings. The brace may further comprise a mating element configured to secure the first layer in a strained configuration on the brace. The brace may be rigid. The brace may comprise a plurality of segments bendable with respect to another of the plurality of segments to provide a variable contour of the brace. The brace may be configured to be bendable in a plurality of directions. Each of the plurality of segments may be configured to be bent in a plurality of directions. The second layer may comprise a mask having a pattern of openings. The pattern of openings comprises a treatment pattern. The skin treatment device may further comprise a connection element configured to connect the device to an energy emitting skin treatment device. Each second layer opening may correspond to at least one individual treatment zone. The second layer may be removable from the first layer after treatment is provided through the at least one second layer opening.

In another variation, a multilayered elastic dressing is provided, comprising a plurality of elastic layers, wherein each layer removably coupled to another layer of said plurality of elastic layers; wherein said plurality of elastic layers comprises a base layer having a skin adhesive layer on a skin adhesive side of the base layer and at least one additional layer. Each said at least one additional elastic layer may be removable from the base layer after the dressing has been strained and adhered to skin of a subject to thereby selectively alter the stresses placed on the skin through the base layer.

In another variation, a method of treating a subject is provided, comprising creating a plurality of lesions on a subject's skin and placing a dressing over the lesions on the subject's skin.

In another variation, a method treating a subject is provided, comprising placing a dressing over a skin region and creating lesions in the skin region through the dressing. Creating lesions in the skin regions may be performed using an energy-based modality. The dressing may comprise a mask region configured to selectively block the energy-based modality and a treatment region configured to selectively permit energy from the energy-based modality to pass through the dressing. The treatment region comprises an uninterrupted structure configured to selectively permit energy to pass through the uninterrupted structure. The uninterrupted structure may be an optically clear structure. The method may further comprise aligning a treatment device to indicia located on the dressing. The method may further comprise aligning a treatment device to pre-existing openings in the dressing. The pre-existing openings may be pre-existing potential openings in the dressing. The pre-existing potential openings may comprise slits. The method may further comprise creating a plurality of openings in the dressing using a treatment device.

In another variation, a method of treating a subject is provided, comprising maintaining a strain in an elastic dressing, placing the strained dressing over skin of a subject, creating at least one lesion on the skin of the subject through the dressing; and then releasing the dressing so that compressive forces from the dressing are applied to the skin of the subject.

A need remains for devices, kits and/or procedures to improve the outcome of such medical procedures by improving the healing process of the tissue subsequent to the treatment.

BRIEF DESCRIPTION OF THE DRAWINGS

FIGS. 1A to 1C illustrate the process of a conventional skin tightening procedure performed on a section of skin.

FIG. 2A illustrates an example of a wound dressing that assists in the healing process to improve the outcome of a cosmetic procedure or provides temporary movement of tissue.

FIGS. 2B to 2D show an example of a dressing assisting in a wound healing process.

FIGS. 14A to 14D illustrate various types of lesions that can be created in situ with a solid dressing.

DETAILED DESCRIPTION OF THE INVENTION

Figure 2E:
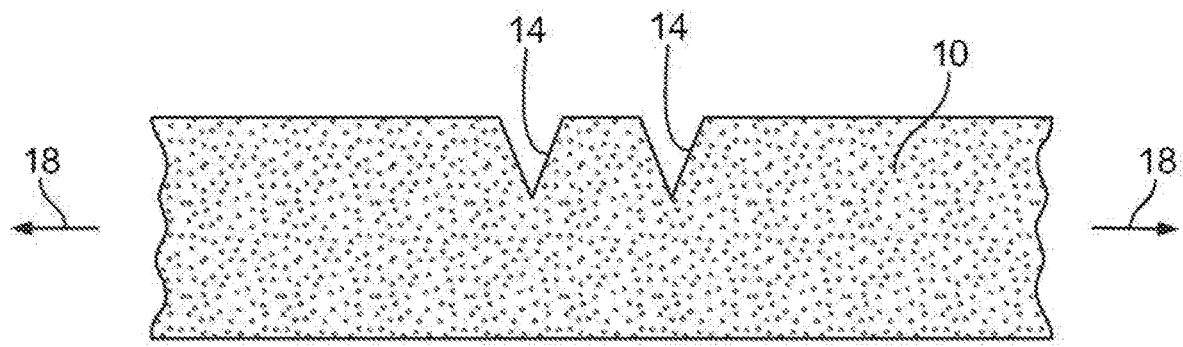
FIGS. 2E to 2G show another example of application of a dressing to assist in the wound healing process.

The methods, procedures, kits, and devices described herein are intended to assist with the healing process of tissue that was previously or simultaneously treated for a therapeutic or cosmetic effect. Assisting in the healing process can produce an improved outcome and in some cases can eliminate or reduce variability with the healing process. The combined therapeutic process of treating tissue and assisting the ensuing healing process can produce a consistent skin tightening procedure and improve the outcome of the procedure. It is noted that combinations of variations of the methods, kits, and/or procedures as well as combination of specific aspects of methods, kits, and/or procedures are within the scope of this disclosure even though such embodiments may not be specifically shown.

U.S. Pat. No. 7,683,234 to Gurtner et al describes devices and methods intended for the amelioration of scar and/or keloid formation and include a discussion of wound healing as well other information that can be combined with the novel methods, devices, and kits of the present invention. Accordingly, the entirety of this reference is incorporated by reference herein.

The present disclosure describes the methods, procedures, kits, and devices for use with skin tightening, treatment of skin laxity, skin contraction, skin shrinkage, and maybe even body sculpting procedures for purposes of illustration. However, the invention is not limited to skin tightening unless specifically noted otherwise. The benefits of the present disclosure can be applied in any number of medical procedures requiring providing augmentation of the healing process of a therapeutic or cosmetic treatment. For example, the devices herein may be used for sutureless wound closure, skin splinting or other supportive uses. Other uses for these skin treatment devices may or may not include without limitation, for example, amelioration or prevention of scar formation, treating skin related conditions such as acne, blemishes, rosacea, warts, rashes (including but not limited to erythematous, macular, papular and/or bullous conditions), psoriasis, skin irritation/sensitivity, allodynia, telangiectasia, port wine stains and other arterio-venous malformations, and ectopic dermatitis; treating or improving existing scars, wrinkles, stretch marks, loose or sagging skin or other skin irregularities; lifting, pinning, holding, moving skin for various purposes such as during pre-operative preparation, during surgical procedures for example as a low-profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may include use of a drug or other therapeutic agent that may be applied to the skin with such device. The agents may include but are not limited to antibiotics, anti-fungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face (e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes.

A number of procedures for tightening of skin are commonly known. One non-invasive approach involves the use of laser energy to ablate (vaporize) or non-ablatively heat the skin. Ablative procedures are generally more invasive (i.e. longer down time) and effective. These types of lasers do not produce consistent skin tightening, and presently none of these lasers are FDA indicated for skin tightening. In general, the procedure relies on a lesion (if an area is treated) or a number of lesions to heal after the injury to produce a tightened appearance in or around the skin that was treated. However, if the holes or lesion made by the treatment device are too large, the skin surface will not heal well. In addition, the procedure might not produce an optimal outcome if the healing process is not consistent between the lesions. Furthermore, care must be taken to prevent environmental factors from interfering with the healing process. Additionally many non-ablative tightening procedures rely on collagen contraction to produce volume changes in the collagen by a thermal denaturation process that produces dimensional changes in skin in one or more axes. See, for example, the RF product THERMAGE® (Solta Corp., Hayward, Calf.) or the IR product TITAN® (Cutera, Inc., Brisbane, Calif.). The devices herein may also be used with other skin treatments (aesthetic or not) or resurfacing procedures whether topical or subdermal, whether or not using an energy modality such as, for example, microwave, radio-frequency ablation, high-intensity focused ultrasound, laser, infrared, incoherent light, thermal (heat and/or cold, ablative or non-ablative), use of vacuum or suction, vibration or massage (e.g. ENDERMOLOGIE®, LPG Systems, France). The methods, kits, and devices described herein can optionally be used with such non-ablative tightening procedures as well. For example, a water jet can be used to create lesions by directing water or other liquid, and/or a mix of liquid and particles to create the lesions. Furthermore, the water or fluid can be used to swell or expand tissue. Once expanded the tissue can be treated such that upon reversion to a normal non-swelled state, the tissue engages in natural compression.

FIGS. 1A to 1C illustrate the process of a conventional skin tightening procedure performed on a section of skin. As illustrated in FIG. 1A, the dermis 10 is located over a region of subcutaneous fat 12. During a skin tightening procedure, as shown in FIG. 1B, a physician creates one or more lesions 14 (i.e., areas of treated tissue or actual openings in tissue) in the dermal region 10. The skin tightening procedure relies on the adjacent healthy tissue to produce a healing response 16 or scar tissue that contracts the adjacent regions of the dermis layer 10 as shown by arrows 18. The purpose of the scar tissue 16 is to create a state of traction for the adjacent region of tissue to produce a tissue tightening effect. The single lesion shown in the figures is for illustrative purposes only. Clearly, the number of lesions 14 created during the procedure will vary. Moreover, the location of the treatment depends upon the particular procedure and region of skin to be cosmetically treated.

In conventional skin tightening procedures, there is variability in the healing phase of the dermis 10. This variability can lessen the desired cosmetic effect. The dressings described herein are intended to reduce this variability and provide an improved effect as a result of the healing process.

FIG. 2A illustrates one example of a wound dressing 100 according to the present disclosure that assists in the healing process to improve the outcome of the procedure. The dressing 100 can have any number of shapes as desired by the intended application. For example, the dressing shown in FIG. 2A has a rectangular shape. However, variations include dressings 100 having contoured shapes to accommodate placement of the dressing around or near various anatomic features. Moreover, the dressing can be cut to fit to a desired anatomic region or to alter the characteristics of the dressing as described below. Alternatively, the dressing can be fit to the desired anatomic region and cut or shaped after it is placed on the region. Exemplary construction and/or material(s) used for the dressing may include those disclosed in U.S. application Ser. No. 12/854,859, filed on Aug. 11, 2010, which was alreadyhereby incorporated by reference in its entirety herein. In some variations, the dressing comprises an elastic material configured with a load per width of at least 0.35 Newtons per mm at an engineering strain of 60% or a load per width of at least 0.25 Newtons per mm at an engineering strain of 45%. The elastic material may have a load per width of no greater than about 2 Newtons per mm at the engineering strain of about 45% to 60%, about 1 Newtons per mm at the engineering strain of about 45% to 60%, about 0.7 Newtons per mm at the engineering strain of about 45% to 60%, or no greater than about 0.5 Newtons per mm at the engineering strain of about 45% to 60%. The elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of about 20% to 30% and attached to a surface. The elastic material may comprise an adhesive configured to maintain a substantially constant stress in the range of 200 kPa to about 400 kPa for at least 8 hours when strained to an engineering strain of about 20% to 30% and attached to a surface. The substantially constant stress may vary by less than 10% over at least 8 hours, or by less than 5% over at least 8 hours.

FIG. 2A shows one variation of a dressing 100. In this example, the dressing can comprise an elastomeric dressing (e.g. fabricated from silicone) that can optionally stretch as shown in directions 102 to expand the dressing 100 to an expanded profile 106. The dressing device 100 can further optionally include any configuration of adhesive 104 to adhere to skin. The adhesive should not prevent the skin and/or the lesions from compressing as described herein. Alternatively, variations of dressings can allow for adhesive to be applied prior to or during application of the dressing on tissue.

The device can be placed on the dermis 10 as shown in FIG. 2B. As discussed below, the dressing 100 can be placed on the dermis 10 either prior to, during, or subsequent to creation of the lesion 14. Once the lesion 14 is created (or during creation of the lesion 14), the dressing 100 applies a closure force F to contract the lesion 14 so that the dressing 100 causes the opening 14 in tissue to close as illustrated in FIG. 2C. The tissue formed 20 as a result of the healing response then maintains the dermis 10 in a state of traction even after removal of the dressing 100 as shown in FIG. 2D. The closure force F can be applied in a single direction/axis or in a planar direction (e.g., X-Y axes). Stretching of the dressing 100 can be uniform or non-uniform depending upon the area of placement. As described below, variations of the dressing 100 can be configured to provide for stretching in pre-determined directions or amounts.

In those variations where the dressing 100 is elastomeric and pre-stretched, the release of the dressing 100 from the stretching force creates the closure force F that is applied on tissue. In alternate variations, the dressing 100 can provide a closure force via thermal, electrical, chemical or other activation of an appropriately configured dressing 100. In such cases, the dressing applies little or no force unless activated.

Figure 3A:
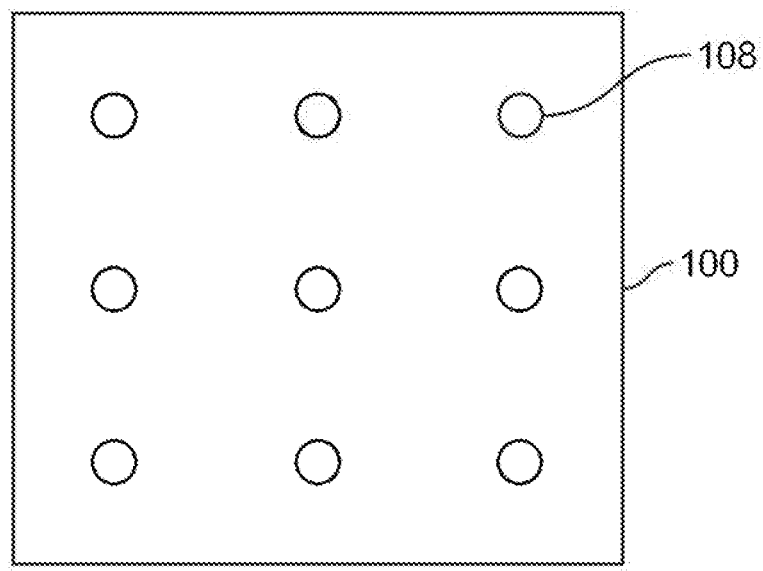
FIGS. 3A and 3B respectively show an expanded or strained dressing and a dressing in an unstrained or relaxed profile.
Figure 3B:
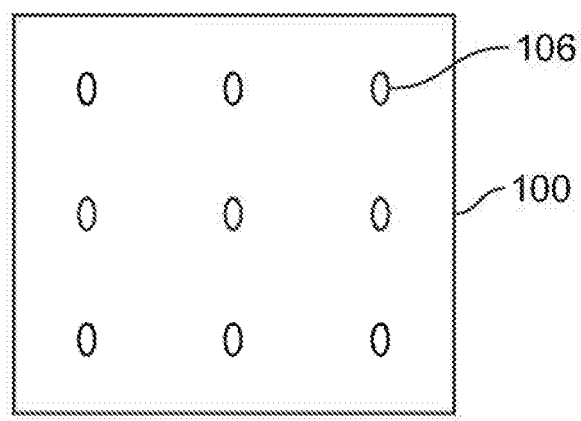

As shown above, the dressing 100 can have openings adjacent to the lesion 14. FIG. 3A illustrates these openings 108 in a dressing 100 where the dressing is strained or expanded. The openings 108 can be pre-made in the dressing 108 or can be created during the application of energy to the tissue. As shown in FIG. 3B, the openings 108 reduce in size or can close when the dressing 100 returns to the compressed or reduced state. The openings 108 can serve an additional purpose of allowing moisture to pass through the dressing 100. Accordingly, variations of the dressing 100 can include additional openings 108 solely allow for passing of moisture through the dressing 100.

The openings may have any of a variety of shapes, including circles, ovals, triangles, square, rectangular, star-shaped, etc. Each of the In some variations, the openings (or a portion of the openings) may comprise potential openings which appear to be slits or cuts in the dressing, which then open or spread apart upon tensioning. FIGS. 3G and 3H depict one example of a dressing 100 in a unstrained and strained configuration, respectively, with openings 108 comprising slits which are transversely oriented to the direction of tensioning, which form double-tapered openings upon straining. The slits or cuts may be linear or curved, isolated or branching, etc.

In some further variations, one or more of the openings may be reinforced with a thicker or non-elastic material to reduce or control excessive strain in the dressing material about the openings, in comparison to regions without openings. In some variations, the reinforcement may comprise open or closed perimeter, ring-like structures surrounding the openings. Materials that may be used for the reinforcement structures include but are not limited to low-density polyethylene (LDPE), fluorinated ethylene propylene (FEP) or nylon. The openings 108 of the dressing 100 may comprise individual reinforcement structures 124, as depicted in FIG. 3I, or a regional reinforcement structure 125 that reinforced multiple openings 108, as depicted in FIG. 3J. In other variations, the reinforcement structure may comprise a layer of material embedded or attached to a surface of the dressing, the layer of material comprising an inelastic material or a material with reduced elasticity relative to the dressing. The layer of material may comprise identical openings, slits or cuts as the dressing, or may have a different configuration. In still other variations, no openings, cuts, or slits are provided in the dressing, but indicia may be provided on the dressing to facilitate the formation of a skin lesion pattern through the dressing. In some variations, the indicia may comprise a uniform graphical grid depicted on the dressing, but in other variations, a non-uniform grid or other non-uniform pattern is provided.

Figure 2F:
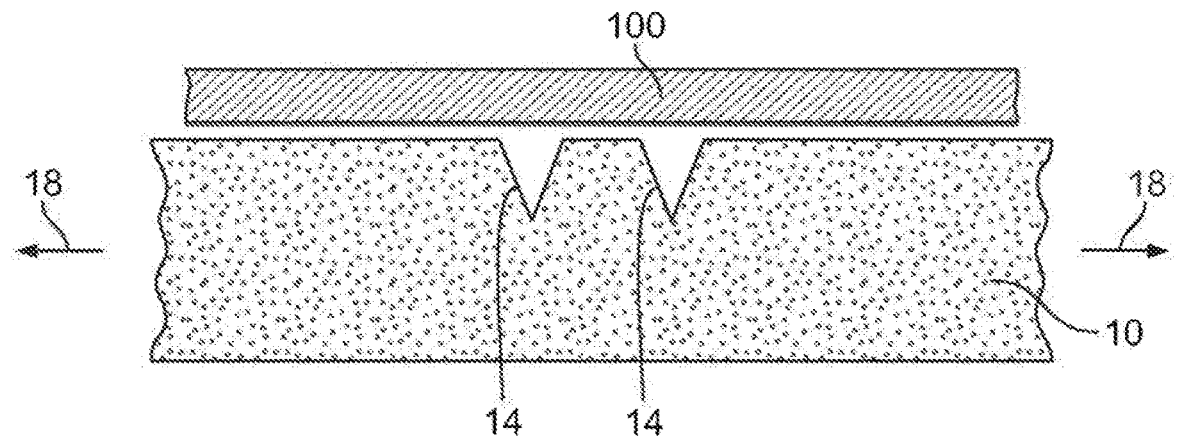
Figure 2G:
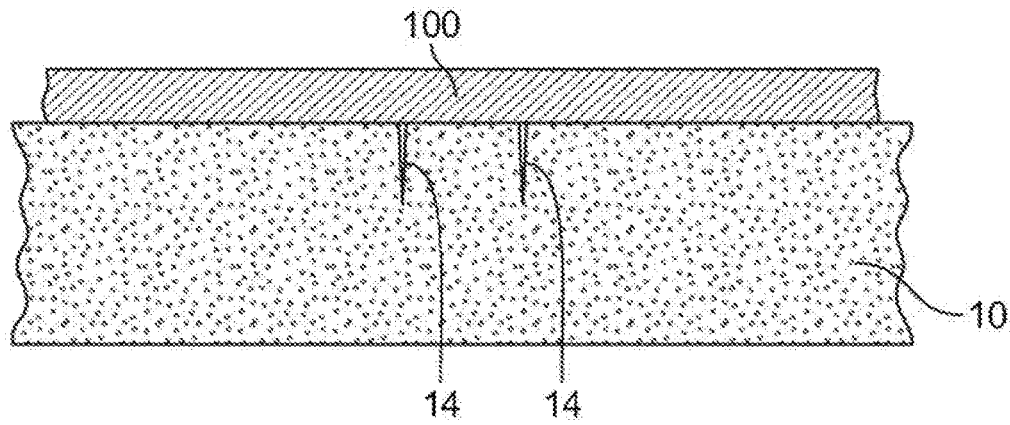

FIGS. 2E to 2G show another variation of application of a dressing 100 for use in the methods and devices described herein. In this variation, as shown in FIG. 2E, the tissue is placed under a state of traction or is strained as shown by application of a straining force 18 and the lesions 14 (or a single lesion) are created. Next, as shown in FIG. 2F, a physician positions a dressing 100 adjacent to or on the region of tissue 10 and over the lesions 14. The dressing 100 can have openings over the site of the lesions 14 or the dressing 100 can be continuous. FIG. 2G shows removal of the strain from the tissue 10 which causes closure of the lesion 14. Once the strain is removed and the tissue relaxes is the dressing adhered to the tissue 10. Adhering of the dressing can occur via an adhesive on the dressing, activation of the dressing, or application of an adhesive between the dressing and tissue.

Figure 2H:
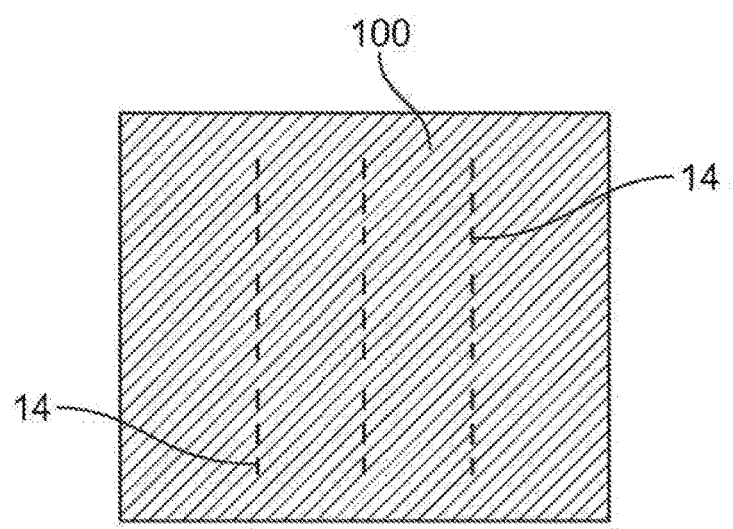
FIGS. 2H and 2I illustrate an example of a second dressing or frame placed upon an initial dressing.
Figure 2I:
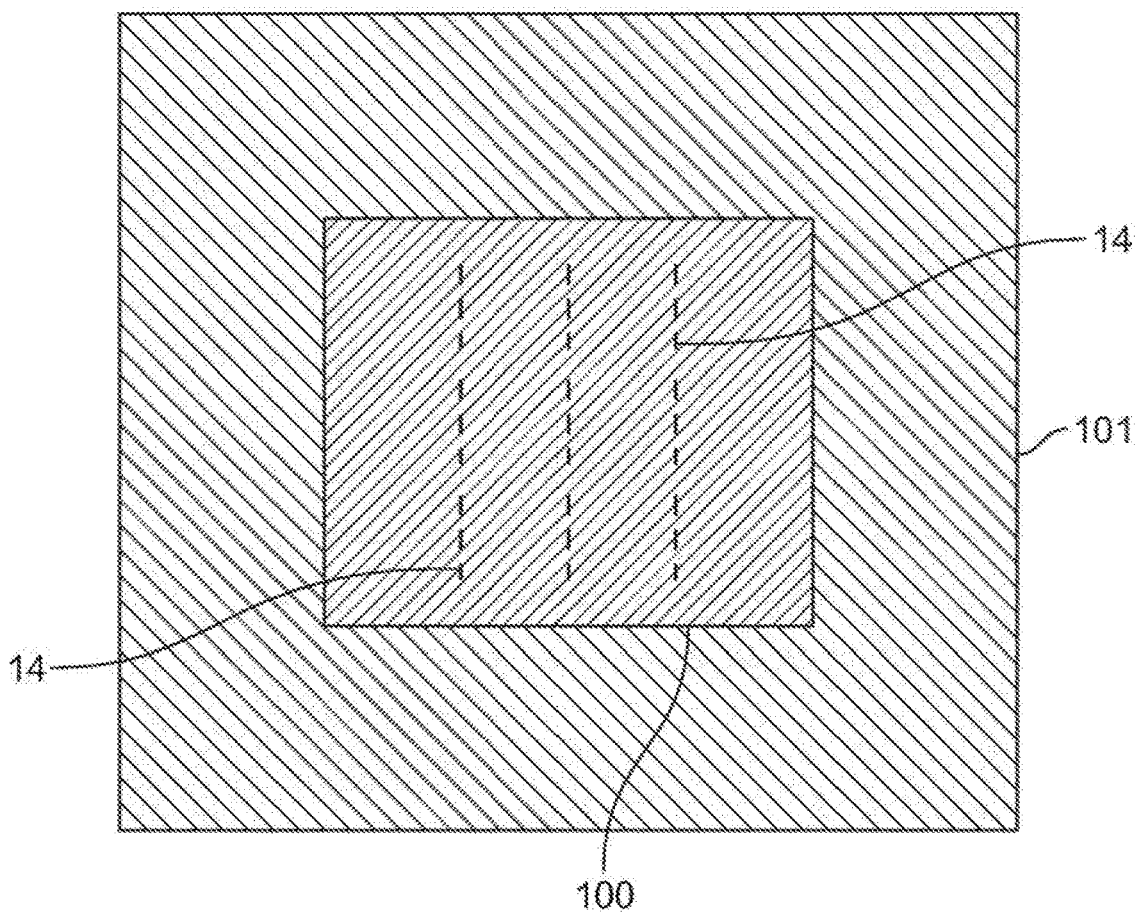

FIGS. 2H and 2I illustrate another aspect of a use of dressings 100 that can be combined with the methods and devices described herein. In this variation, a dressing 100 is placed upon one or more lesions 14 as described herein. However, a second dressing or frame 101 is positioned to overlap the first dressing 100.

The dressing 100 can be retained on the skin by any number of mechanisms. For example, some variations include an adhesive located between the skin and dressing. Alternate variations include the use of a tape or other sealing means placed around or at edges of the dressing 100. The use of mechanical fasteners, e.g., staples, sutures, etc. is also within the scope of this disclosures.

Figure 3C:
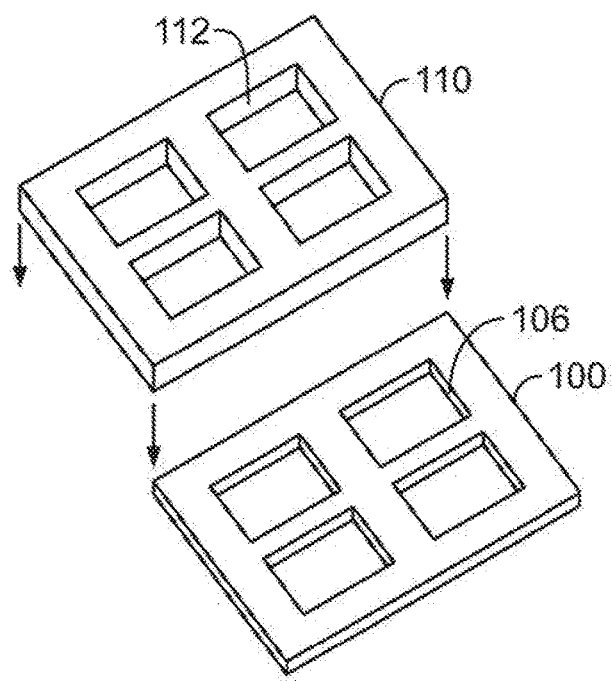
FIGS. 3C to 3F show additional variations of dressings.

FIG. 3C illustrates another variation of a dressing 100 under the present disclosure. In this variation, the dressing comprises a stretchable layer as discussed above with any number of optional window or openings 106. Once the dressing 100 is stretched, a frame or brace 110 can be applied to the dressing 100 to maintain the dressing 100 in the stretched configuration. This may be accomplished through a fastening system (e.g., clamps or teeth) or via a temporary adhesive. The brace 110 can include any number of windows or openings to provide an unobstructed path to the tissue to create the lesions. Once the treatment occurs, the brace 110 can be removed from the dressing 110 to permit the dressing 100 to compress the lesions. In some variations, the brace 110 comprises a flexible but inelastic or incompressible material configured to resist a compression load per millimeter width of at least about 0.1 Newtons, about 0.2 Newtons, about 0.3 Newtons, about 0.4 Newtons, or about 0.5 Newtons, or more. In still other variations, the brace 110 may comprise a malleable material or a substantially inflexible or rigid material. In further variations, in the brace 110 may be pre-shaped with a generally planar shape, but in other variations, may be pre-shaped to a semi-cylindrical or other arcuate shape along one dimension of the brace 110.

Figure 3D:
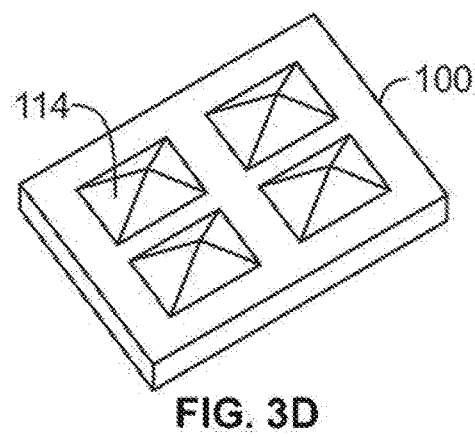
Figure 3E:
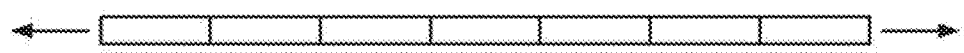
Figure 3F:
Figure 3G:
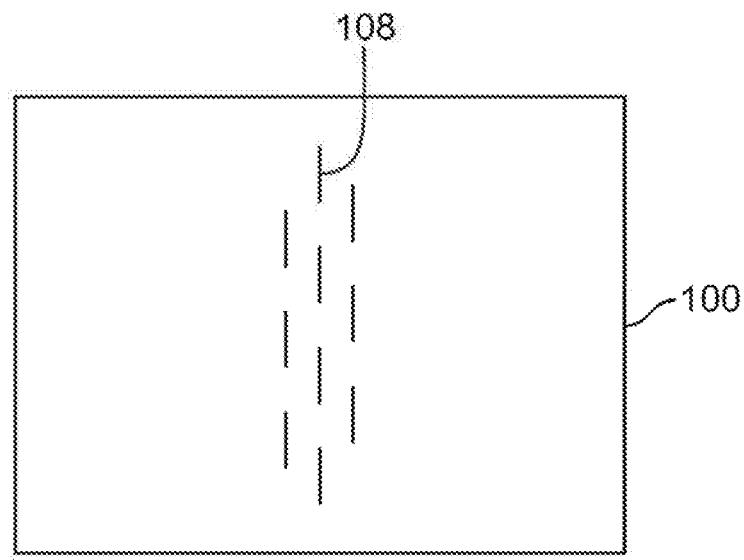
FIGS. 3G and 3H respectively depicted a dressing with slit openings in an unstrained and strained profile.
Figure 3H:
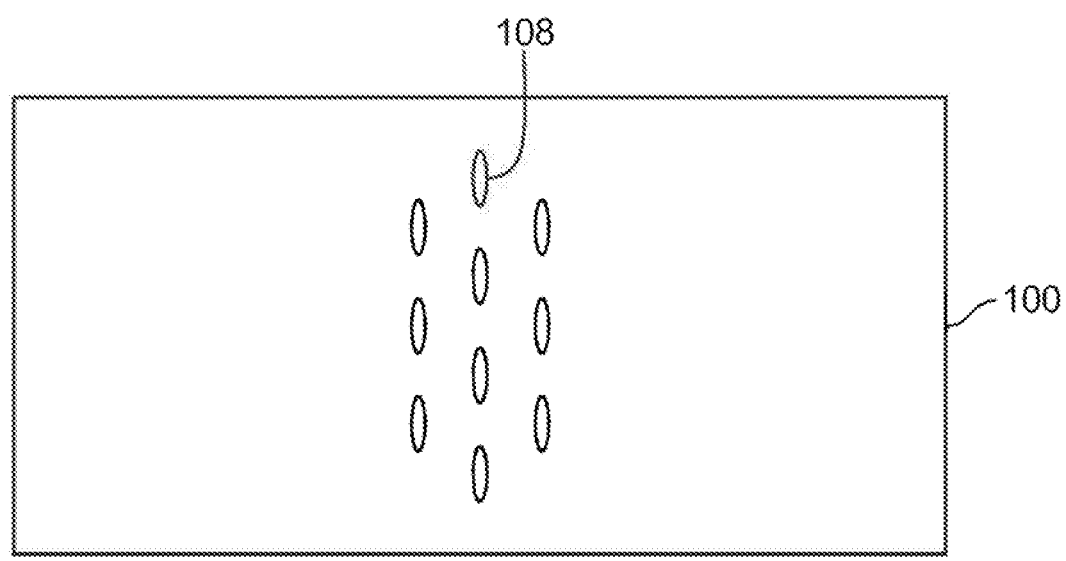
Figure 3I:
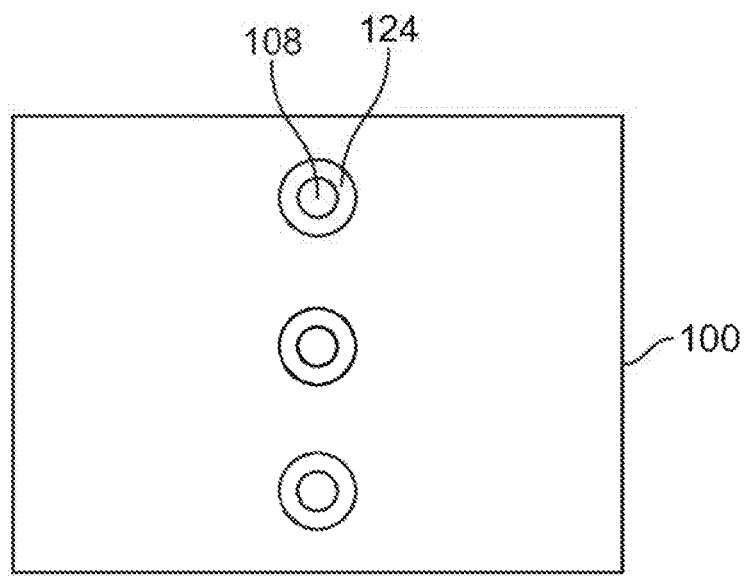
FIGS. 3I and 3J depict additional variations of dressings with reinforced openings.
Figure 3J:
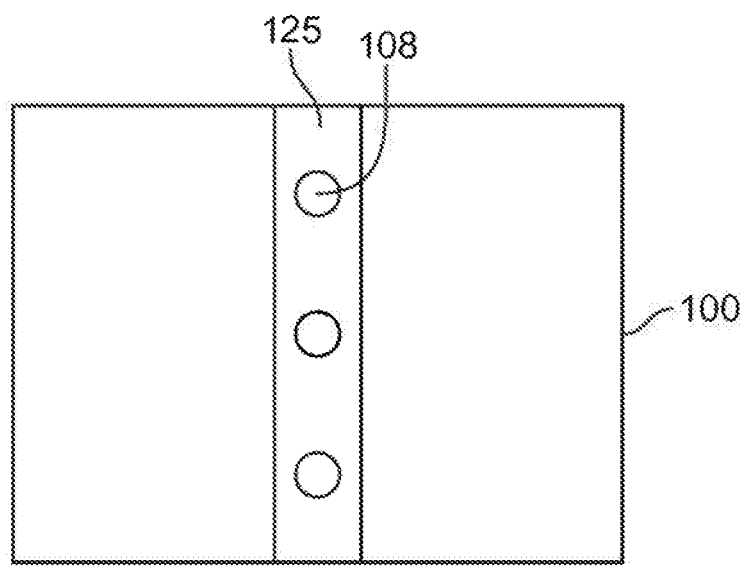

FIGS. 3D to 3F show another variation of a dressing 100. In this variation, instead of openings, the dressing 114 includes any number of raised surfaces 114. Prior to application on tissue, this variation of the dressing 100 is stretched out, as shown in FIG. 3E. When applied to tissue the dressing 100 reverts to its pre-stretched shape so that the raised surfaces 114 separate from the surface of the tissue as shown in FIG. 3F. In such a variation, adhesive can be applied to the planar portion of the dressing 100 around the raised areas 114.

Any of the dressings 100 shown above (and/or braces) can be mated or aligned with the lesion-creating device so that the dressing can be applied with a single device. Alternatively, a number of dressings 100 can be fitted to the treatment device in a cartridge-like form so that the physician can position a dressing onto the treatment device prior to application of the device to tissue.

Figure 4A:
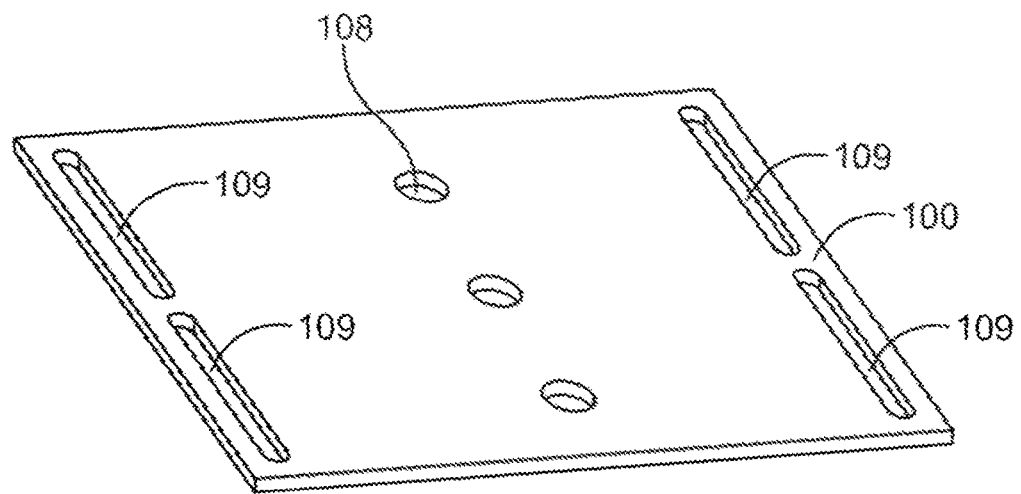
FIGS. 4A and 4B illustrates a dressing and frame respectively, where the frame maintains the dressing in a strained configuration for eventual placement on tissue.
Figure 4B:
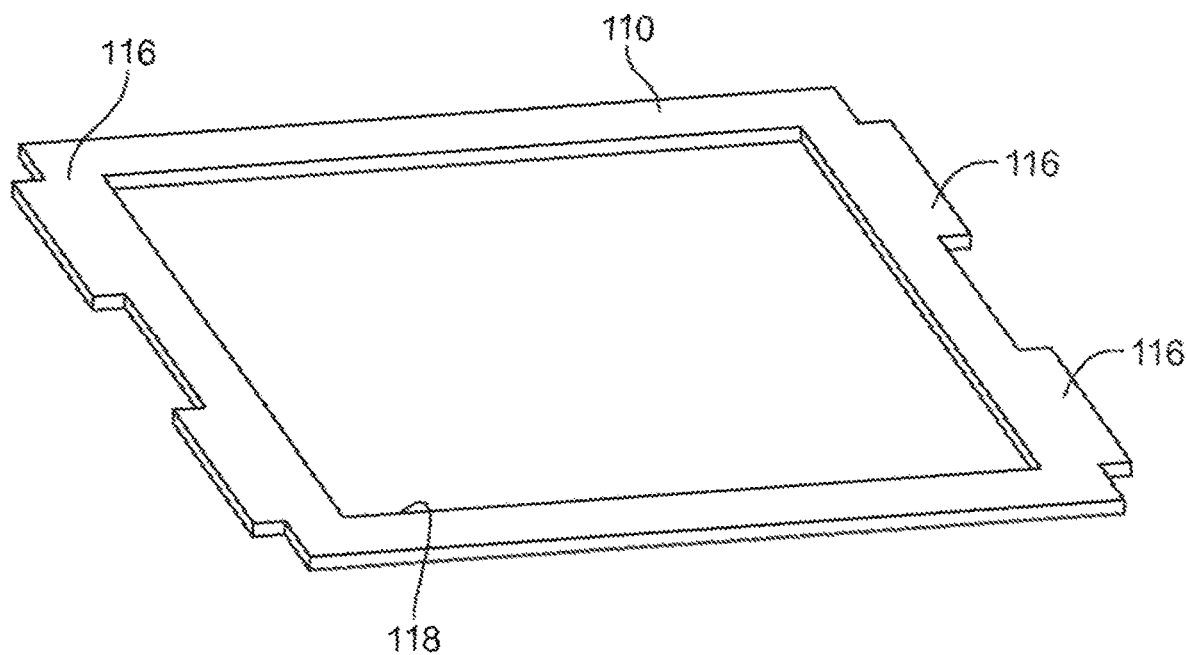

FIG. 4A illustrates another variation of a dressing 100 for use as described herein. In this variation, the dressing 100 includes any number of openings 108 that allow for creation of the lesions. In additional variations, the dressing 100 may not have any lesion-openings 108. In such a case, the treatment could take place through the dressing 100 or the openings 108 could be created after the treatment. In any case, this dressing variation includes one or more retention openings 109. The retention openings 109 are designed so that the dressing can be stretched over a mask or brace 110 as shown in FIG. 4B. The brace 110 will include a number of mating retention tabs 116 so that the dressing can be stretched across the brace 110 and retained on the tabs 116. In this variation, the brace 110 includes a single central opening 118. However, as described above, the brace 110 can include any number of openings (i.e., to match the openings on the dressing, or to provide structural rigidity to allow for stretching.) Typically, the brace 110 is stiff or inflexible when compared to the dressing 100. However, variations can include a brace 110 that is stiff when compared to the dressing 100 but is malleable so that the brace can conform to the contours of a targeted region of tissue. As mentioned previously, the lesion-openings 108 (or other drainage or access openings of the dressing) may be individually reinforced or regionally reinforced to reduce or control any relative greater strain that may occur in regions with openings 108 in comparison to regions of the dressing 100 without opening. As depicted in FIG. 4F, the retention openings 109 of the dressing 100 may also be reinforced with a reinforcement structure 126, which may facilitate manual stretching and attachment of the dressing 100 to the brace 110 by the user. Reinforcement of the retention openings 109 may be beneficial reducing excessive straining of the dressing region 127 between the retention opening 109 and the closest adjacent edge 128 of the dressing 100.

Figure 4C:
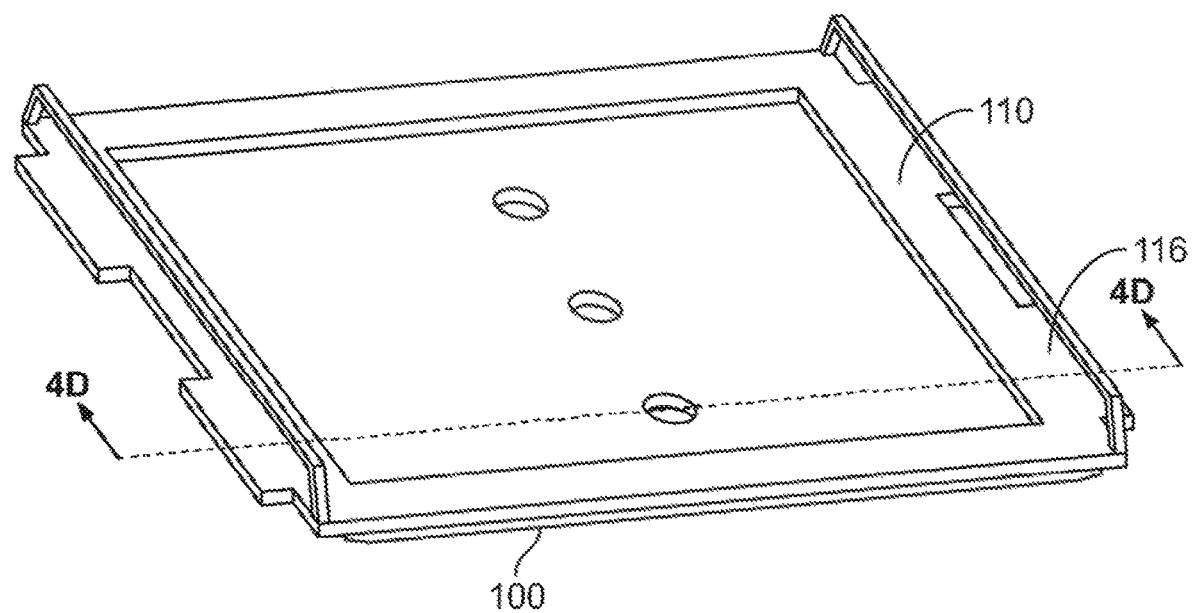
FIG. 4C shows the dressing of FIG. 4A positioned on the frame of FIG. 4B.
Figure 4D:
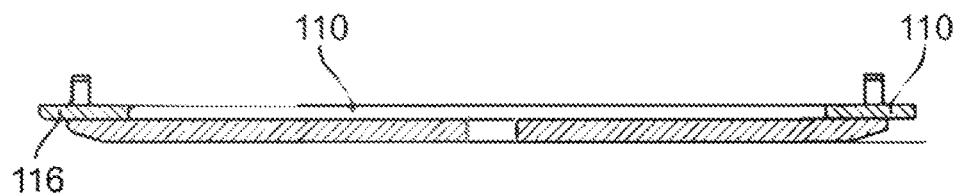
FIG. 4D shows a cross sectional view taken along the line 4D-4D of FIG. 4C.
Figure 4E:
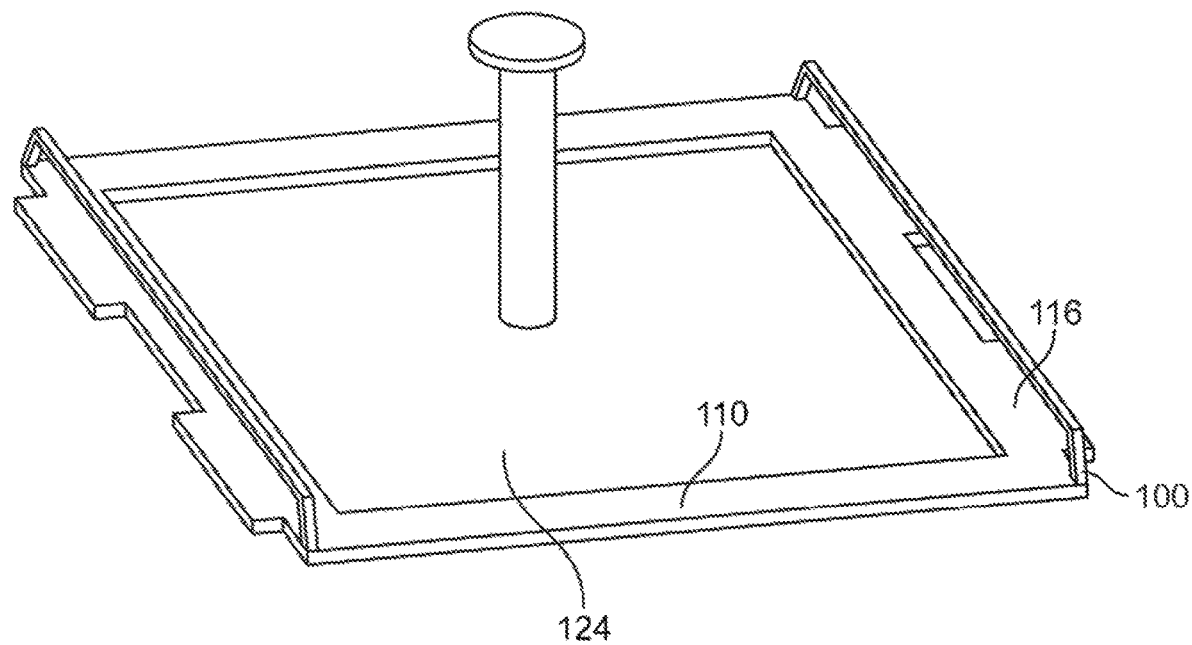
FIG. 4E illustrates an optional applicator used to assist in positioning the dressing of FIG. 4A from a frame to tissue.
Figure 4F:
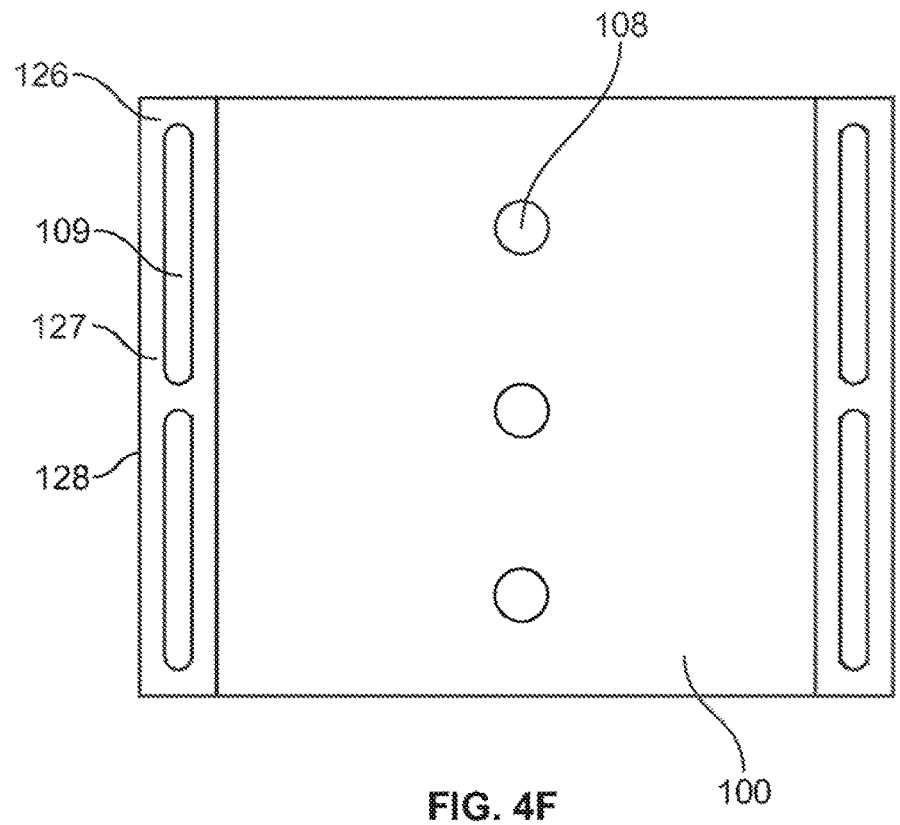
FIG. 4F depicts a dressing with reinforced retention openings.

FIG. 4C illustrates the dressing 110 stretched across the brace 110 with the retention tabs 116 inserted into the retention openings 109 of the dressing 100. FIG. 4D illustrates a cross sectional view taken along the line 4D-4D from FIG. 4C. To release the dressing 100 from the brace 110, the ends of the dressing 100 can be pulled away from the brace when the dressing engages tissue. As discussed herein, the dressing 100 can include an adhesive to secure the dressing onto tissue. Alternatively, an adhesive or other fastening means can be applied to the dressing when the physician places the dressing on tissue. FIG. 4E illustrates a variation of a dressing 100 located on a frame 116 with an applicator that can be used to secure the dressing 100 against tissue as the dressing 100 is released from the retention tabs 116.

Figure 5A:
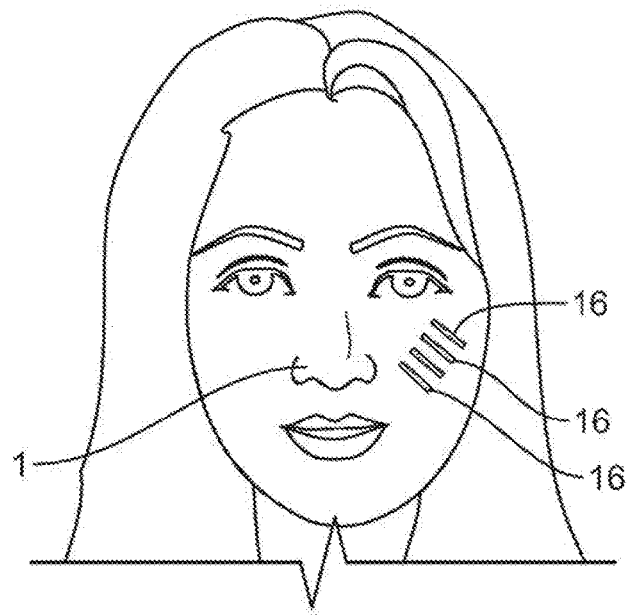
FIGS. 5A to 5C illustrate another variation of a dressing according to the present disclosure.
Figure 5B:
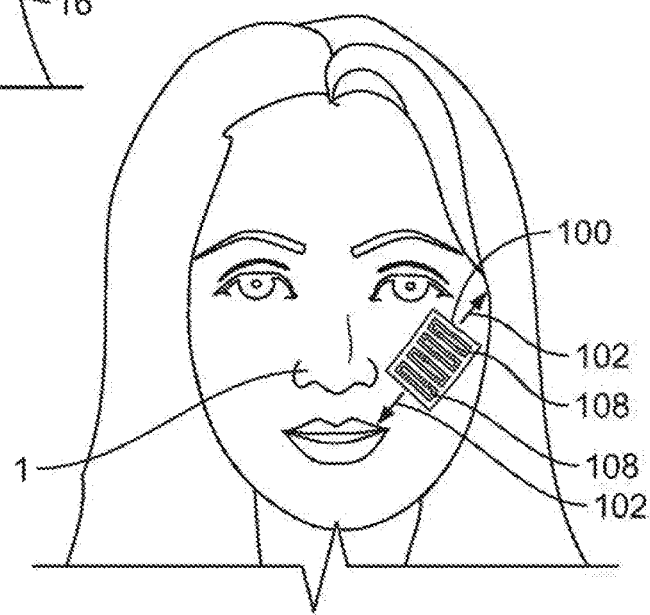
Figure 5C:
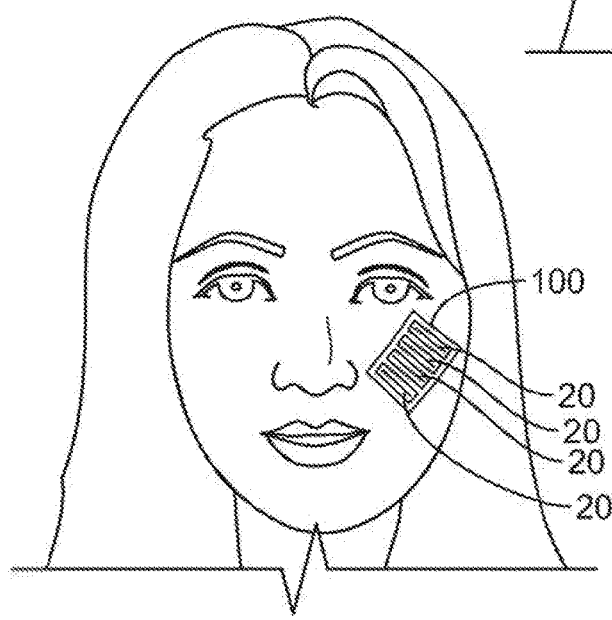

FIGS. 5A to 5C illustrate another variation of a dressing 100 according to the present disclosure. In this variation, the dressing can be configured to provide a uni-axial compression (compression along one axis) where required or a unidirectional compression (i.e., movement of the dressing occurs in a pre-determined direction). FIG. 5A shows a series of lesions 16 created on a face 1 of a patient. In this example, the therapeutic procedure creates the lesions 16 in a line array type pattern as opposed to a plurality of points or dots, where the lines of lesions 16 are arranged or aligned in a pre-determined direction. For example, the pattern can be made in alignment with, against, and/or orthogonal to Langer's lines, also referred to as cleavage lines. Langer's lines are topological lines drawn on a map of the human body. These lines correspond to the natural orientation of collagen fibers in the dermis and epidermis and can be defined by the direction in which the skin of a human cadaver splits when struck with a sharp point. In practice, a series of dressing can be applied with differing orientations corresponding to typical or mapped Langer's Lines.

For example, the physician can create lesions aligned to a directional path that is similar to sutures that could be used to tighten the tissue. FIG. 5B illustrates a dressing 100 stretched in direction 102 and having a plurality of openings 108 that open along the stretched direction. As discussed above, the dressing 100 can include an adhesive for securing to tissue. Alternatively, the adhesive can be applied between the skin and dressing or another mode of fixation can be employed. FIG. 5C shows the dressing 100 upon reaching a pre-stretched or relaxed state. As shown, the openings 108 reduce in thickness to compress the lesions when forming the tissue 20 generated as a result of the healing process.

In another variation, a dressing 100 can be adhered to tissue or skin without significantly stretching and then is stretched. Stretching the tissue in this manner uniformly and gently stretches the skin underlying the dressing in a direction along Langer's lines along with the dressing.

When the skin is then treated through the dressing in a stretched condition, releasing the stretch as well as removing the dressing will allow a gentle closure force due to the skin's own natural elasticity. Presently, physicians stretch tissue using their fingers to stretch the tissue area as they treat. However, this process increases overall procedure time since the physician is only able to treat small areas at any given time. A variation of present invention includes a dressing that is stretched after being applied to the skin to stretch the skin along Langer's lines. Once the tissue is treated, the dressing is removed. This permits the natural resiliency of the skin to provide a gentle closure force without having to leave the dressing in place.

Figure 6A:
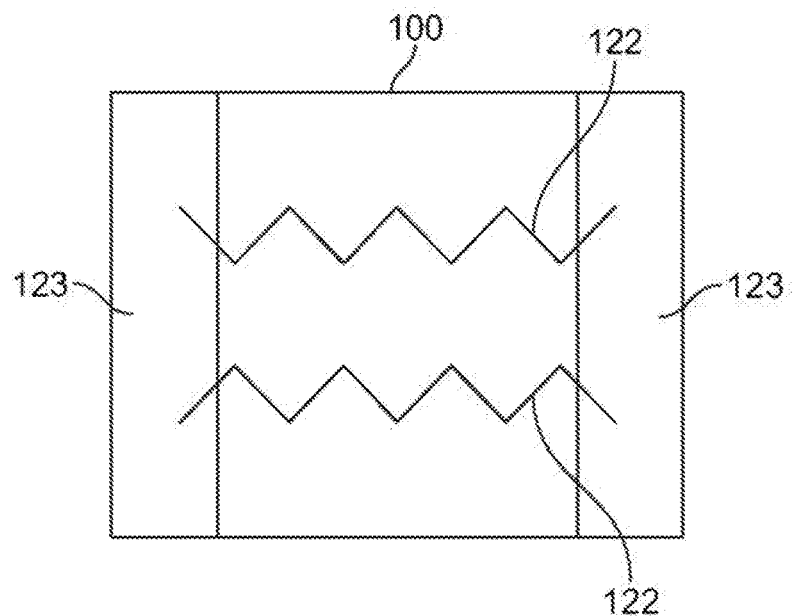
FIGS. 6A and 6B shows a dressing having one or more limiting members to pre-determine a strain capacity of the dressing.
Figure 6B:
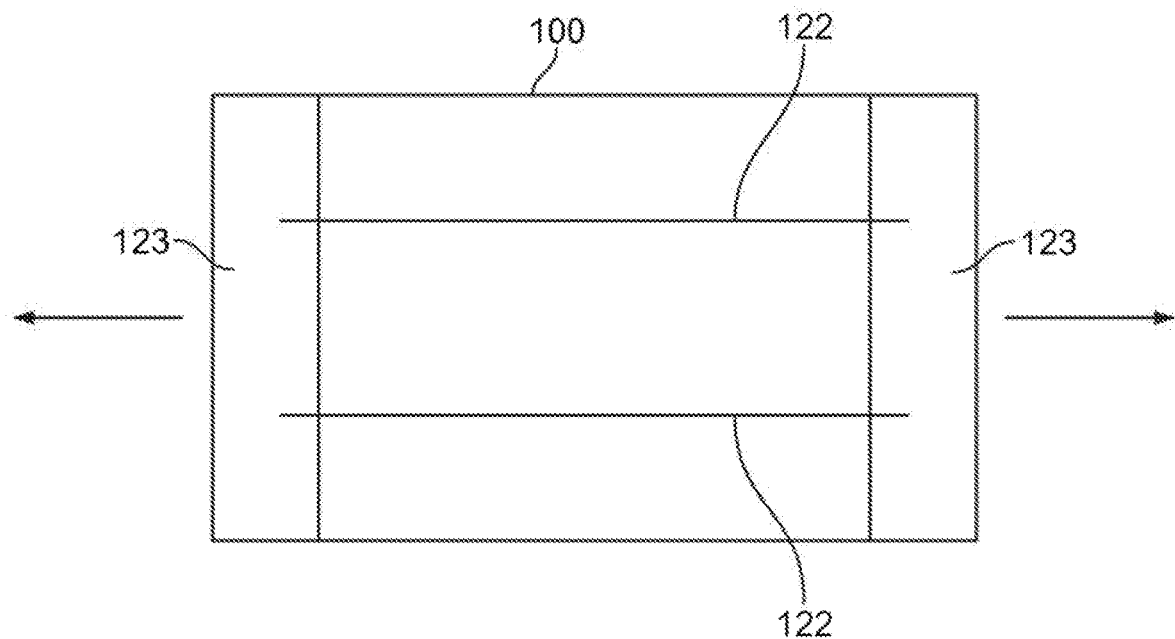

FIGS. 6A and 6B illustrate an aspect of dressings 100 described herein. In this example, the dressing 100 includes one or more limiting members 122 to pre-determine a strain capacity of the dressing 100. For example, as shown in FIG. 6A, the limiting members 122 are shown in a compressed configuration. When the dressing is stretched, as shown in FIG. 6B, the limiting members 122 approach their predetermined length to limit the maximum strain of the dressing 100. Accordingly, a physician can be provided with a number of dressings 100 each having a varying amount of maximum strain. Although FIGS. 6A and 6B illustrate a dressing having uni-directional strain or deflection, variations of the invention contemplate limiting members that limit strain in a bi-axial direction. The limiting members 122 can be comprised of a shape memory alloy such as a super-elastic alloy or a heat activated alloy that extends or contracts in response to a temperature shift. Although a zig-zag shape is depicted for the limiting member 122 in FIG. 6A, in other variations, the limiting member may comprise an undulating configuration or other curved configuration, or any non-linear configuration. The limiting member may comprise any of a variety of relaxed threads, strings, wires or other elongate, elongatable, straightenable or stretchable members that straighten, lengthen and/or stretch to a desired amount, degree, and/or preset limit. The limiting members may be configured with a sufficient tensile strength to prevent, resist or otherwise control over-stretching of the dressing. The skin treatment device may be constructed of multiple layers of an elastic material such as silicone with an adhesive between layers to which the members are attached initially in the relaxed, undulating, sinusoidal, unstraightened or other unstretched configuration. According to a variation, the shape limiting strings or other devices may prevent straining in regions where straining or less strain is desired. For example, the threads may be straight at the edges of the skin treatment device to prevent straining at the edges. In some variations with multiple limiting members, the limiting members may be equally spaced apart and have uniform lengths and uniform attachment points across a transverse dimension to the tensioning axis of the dressing. In other variations, the limiting members may have a variable or non-uniform spacing, may have non-uniform lengths, non-uniform attachment points, and may also be serially arranged along the tensioning axis. The opposing ends of the limiting members 122 may also optionally have removable (or non-removable) manipulation elements 123 attached to the ends to provide for a more even or uniform strain, and may comprise an inelastic material which is the same or different as the limiting members 122. The manipulation elements 123 may span the entire transverse dimension of the device 100 to the axis of tensioning, as depicted in FIGS. 6A and 6B, but in other variations may be less than the entire transverse dimension (e.g. having a transverse dimension sufficient to span a plurality of limiting member 122, but less than the full transverse dimension of the dressing 100. Such elements may comprise planar members, handle members, flexible members and/or inflexible members. They may be attached and removed in a variety of manners, for example as described herein.

Figure 6C:
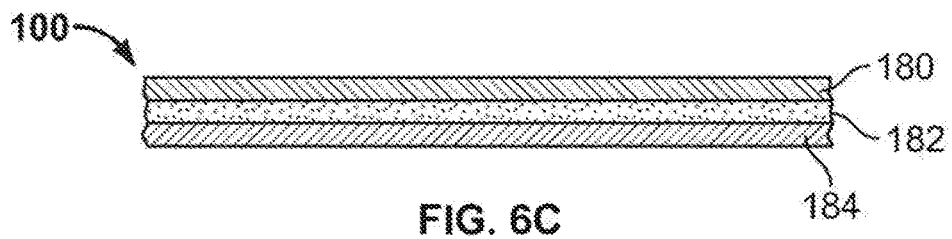
FIGS. 6C and 6D illustrate a variation of a dressing that incorporates a bio-active substance that is intended for delivery to or near the site of the lesion.
Figure 6D:
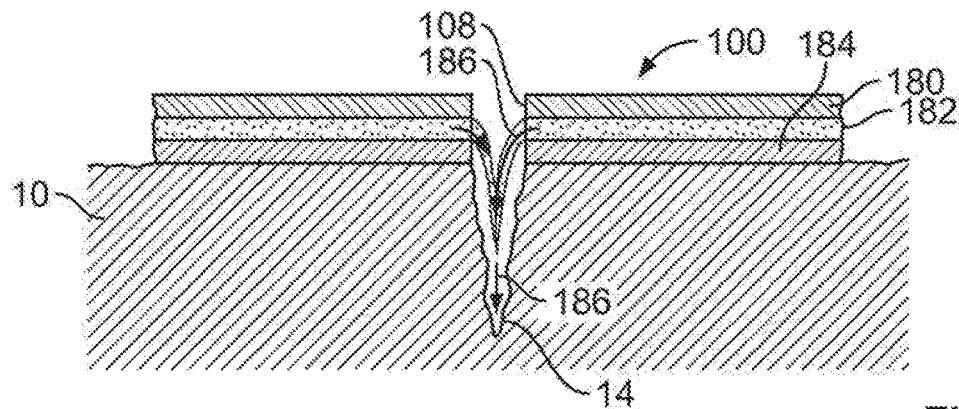

FIG. 6C illustrates another variation of a dressing 100 that incorporates a bio-active substance that is intended for delivery to or near the site of the lesion. In one example, the dressing 100 includes a polymer layer (e.g., silicone) and an adhesive layer 184. The dressing 100 can also include a bio-active substance 182. Although the bio-active substance is shown as a separate layer 182, variations of the dressings can include a bio-active substance that is infused with the polymer layer 180 and/or adhesive layer 184. Alternatively, the bio-active substance can be a separate layer. FIG. 6D illustrates the dressing 100 of FIG. 6C after an opening 108 is made in the dressing 100 during creation of a lesion 14. As shown, creation of the opening causes the bio-active substance to enter the lesion 14 as represented by arrows 186. The bioactive substance can be an activated substance, such as a Rose Bengal dye (a photosensitive dye typically used to cross-link collagen and is activated by light having wavelengths of 514 nm, 532 nm or 458 nm). Alternatively, the bioactive substance can be any drug or pharmaceutical substance delivered for a particular effect on the lesion or tissue. In further examples, the substance can be a material that causes cross-linking of collagen, such as riboflavin and/or glucose. Examples of other bio-active agents that may be used include hemostatic or coagulative agents to help reduce bleeding. Such agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antifibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other active agents that may be useful in aiding in some aspect of the wound healing process. For example, the active agent may be a pharmaceutical compound, a protein (e.g., a growth factor), a vitamin (e.g., vitamin E), or combinations thereof. A further example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin. Of course, the devices may comprise more than one medicament or agent, and the devices may deliver one or more medicaments or agents.

Figure 6E:
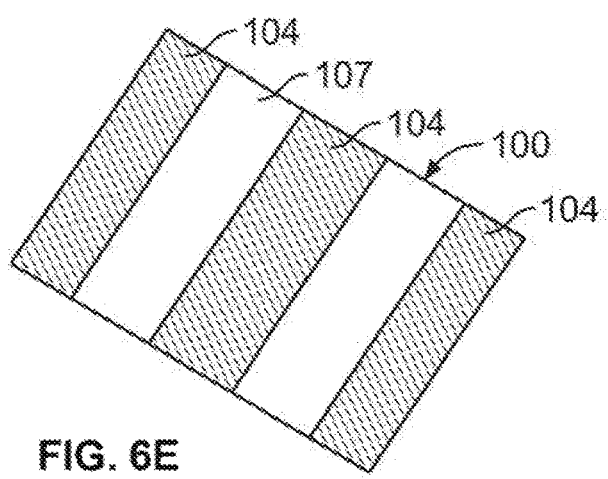
FIGS. 6E and 6F show a variation of a dressing having a varying adhesive pattern on the dressing.
Figure 6F:
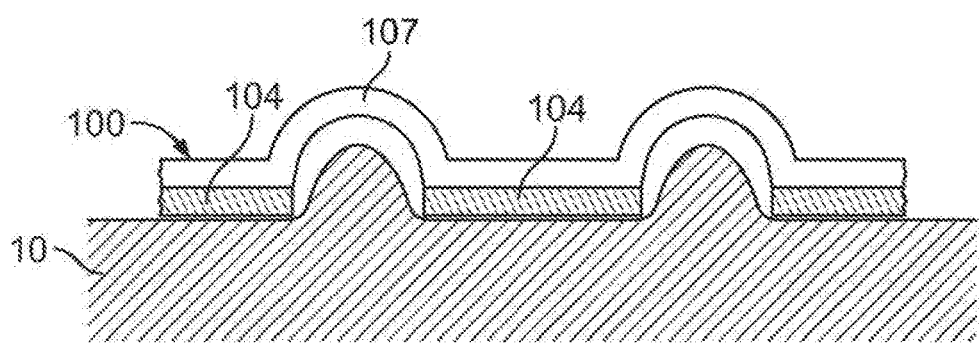

FIGS. 6E and 6F show another variation of a dressing 100 having an adhesive pattern 104 that varies on the dressing 100 as opposed to being located on the entire surface of the dressing 100. FIG. 6E shows one example of a varying adhesive pattern 104 where the adhesive layers alternate with uncovered sections 107. When applied to tissue 10 and released from the strained condition, the dressing 100 contracts at the uncovered regions 107 causing the tissue 10 to buckle at the uncovered regions 107 as shown in FIG. 6F. Other examples of variable adhesive patterns on the dressing are described in U.S. Pub. No. 2011/0152738, filed on Aug. 11, 2010, which was already incorporated by reference in its entirety herein.

Figure 6G:
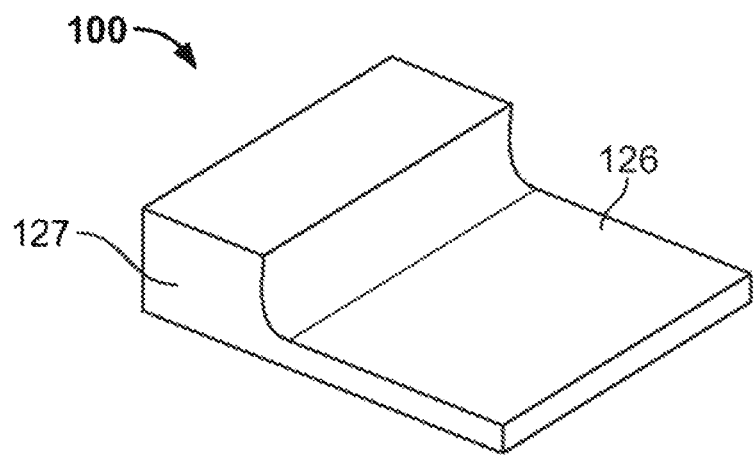
FIGS. 6G and 6H show a dressing that has regions of varying elasticity or stretchability.
Figure 6H:
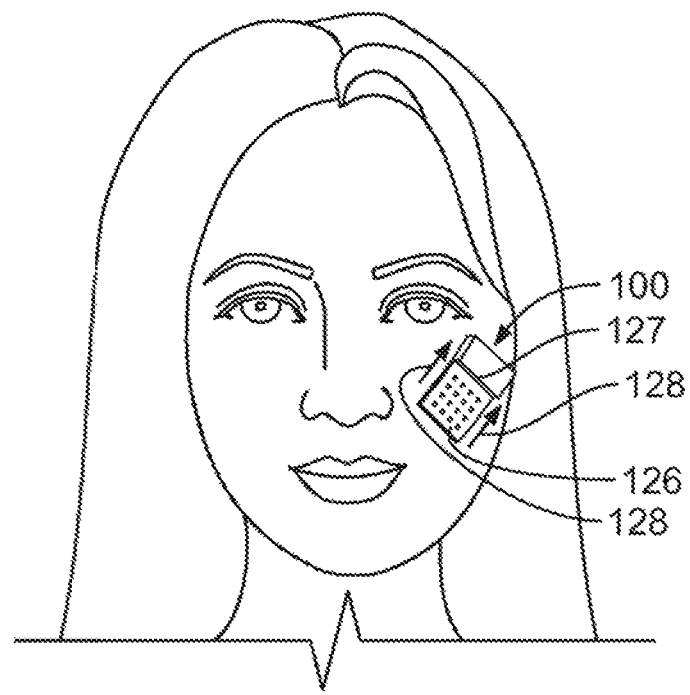

FIG. 6G shows another variation of a dressing 100 for use as described herein. In this variation, the dressing comprises a varying elasticity across different sections. For example, as shown, a dressing can have an elastic section 126 coupled to a relatively less-elastic section 127. The illustrated variation shows the elastic section 126 as being thinner than the less-elastic section 127. However, any number of configurations can provide varying stretch or elasticity. For example, the different sections can have different reinforcements, different materials with varying durometers. One such use of the varying dressing 100 is shown in FIG. 6H, which shows the less elastic section 127 placed in an area where stretching of the skin is not desired and the elastic section 126 being used to produce a pulling force in a desired direction as shown by arrows 128. Other examples of dressings with variable elasticity regions are described in U.S. Pub. No. 2011/0152738, which was already incorporated by reference in its entirety herein. In one particular example, a dressings may be tapered near its edges to reduce thickness. A tapered edge may also ameliorate peak tensile forces acting on skin tissue adjacent to the adhesive edges of the dressing. This may or may not reduce the risk of skin blistering or other tension-related skin trauma. In other variations, the edges of the dressing may be thicker than the middle of the dressing. It is hypothesized that in some configurations, a thicker dressing edge may provide a relative inward shift of the location of the peak tensile forces acting near the dressing edge, compared to dressings of uniform thickness.

Figure 6I:
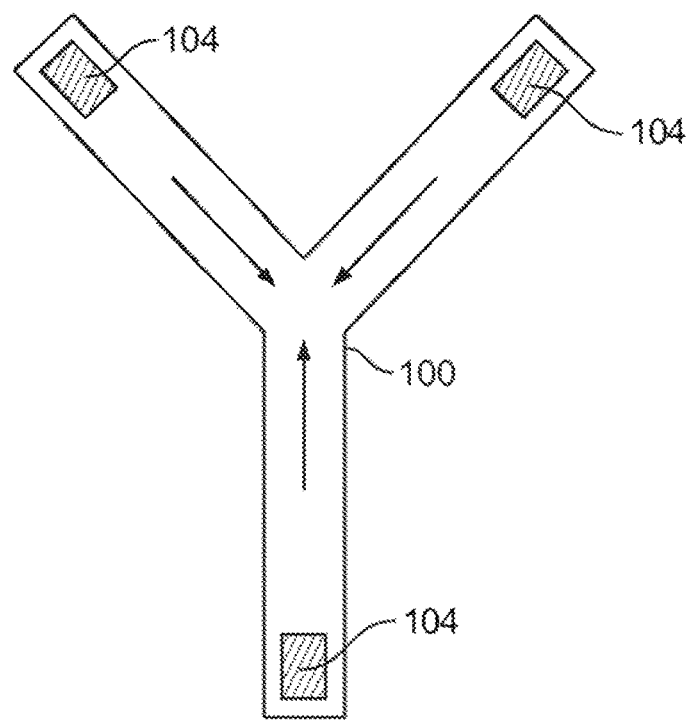
FIGS. 6I to 6K show additional variations of dressings that provide directional or vectored application of force.
Figure 6J:
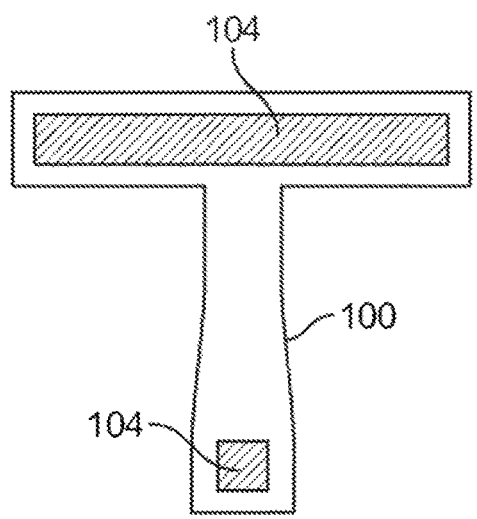
Figure 6K:
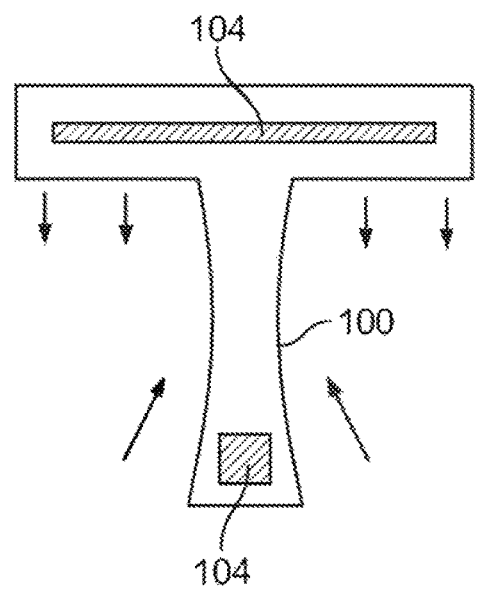

FIGS. 6I to 6K show additional variations of dressings 100 that provide directional or vectored application of force. As shown, the dressings 100 can include adhesive 104 such that when applied to tissue the dressing is pulled to provide a strain in tissue in a desired direction. Benefits of such a variation include providing the physician with control over the degree of strain. Furthermore, the dressings can be treated with, for example, a chromophore to monitor the degree of strain in the dressing. Other examples of a color change material or structure that may be used or incorporated into the dressing are described in U.S. Pub. No. 2006/0246802 to Hughes et al, which is herein incorporated by reference in its entirety.

Figure 7A:
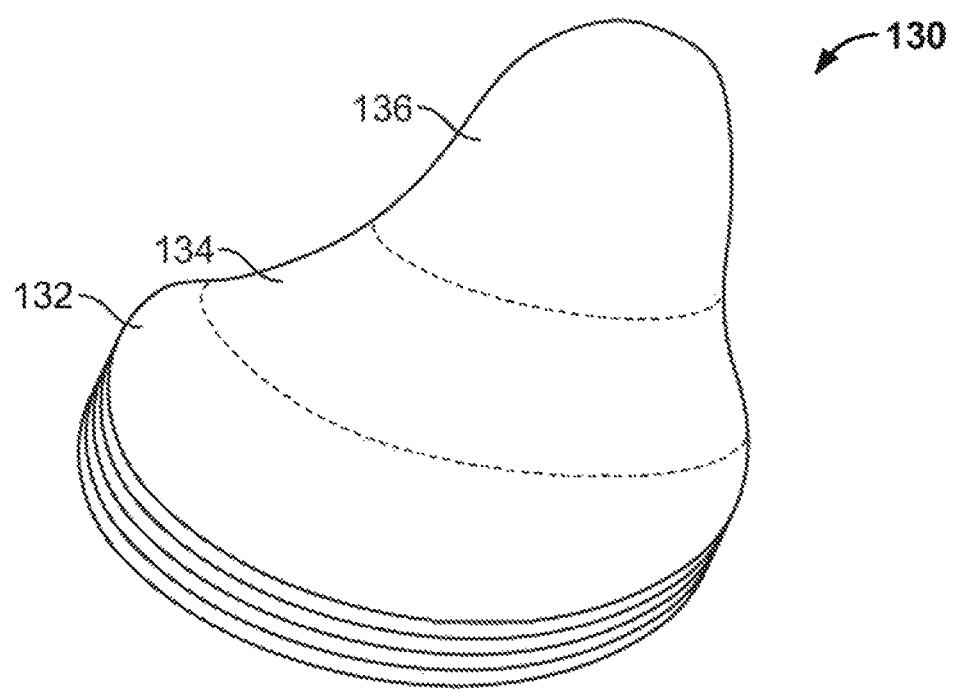
FIG. 7A illustrates a contoured shape multi-layer dressing having regions of varying thickness to allow for customization of a strain amount of the dressing.

FIG. 7A illustrates another variation of a dressing 130 that includes a contoured shape for suited for placement on specific anatomy (for example, the illustrated dressing 130 can be placed on a face of a patient having a larger area at a lower region to accommodate placement along the jawline and a smaller surface area at a top region to accommodate placement close to the ear). FIG. 7A also illustrates the dressing 130 as having a varying thickness across the length of the dressing 130. The varying thickness allows for a physician to adjust the amount of strain that the dressing 130 applies to tissue. For example, section 132 can include the greatest number of layers, which translates into the highest strain rate. To reduce the strain rate, the physician or medical practitioner would cut or remove section 132 from the dressing 130. Removing section 132 leaves sections having fewer layers and as a result, lower strain rates. Although the figure illustrates three sections 132, 134, 136, any number of sections is within the scope of this disclosure.

Figure 7B:
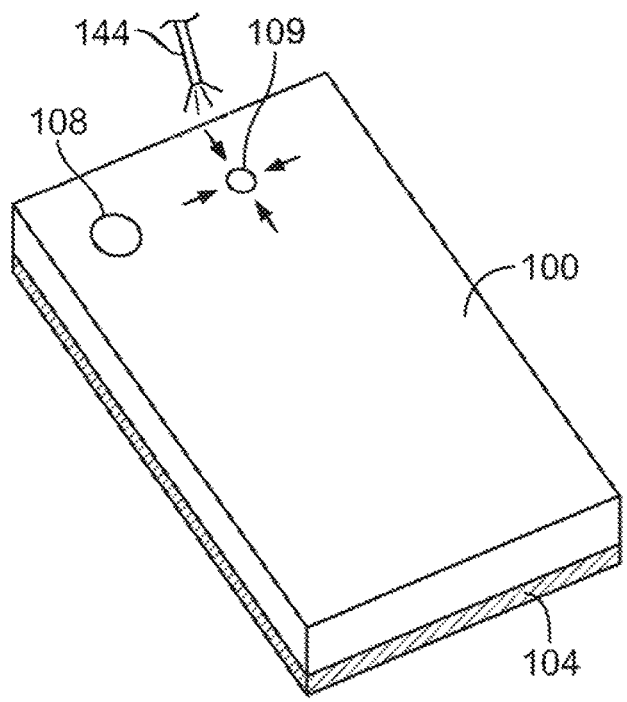
FIG. 7B illustrates a further variation of a dressing that includes a thermally responsive material.

FIG. 7B illustrates a further variation of a dressing 100 that includes a thermally responsive material. In this variation the dressing 100 can include one or more openings 108 but the construction of the dressing 100 allows for customization of the location as well as degree of strain that the dressing 100 will apply on tissue. The dressing can be adjusted using visible or UV light, or it can be activated using a chemical response or via heat. The dressing can also include a separate layer that drives shrinkage of the dressing upon activation (e.g., via a laser, heat, other irradiation). In any case, use of a shrinkable dressing permits customization to create tension or strain in a desired direction during the treatment procedure.

Figure 7C:
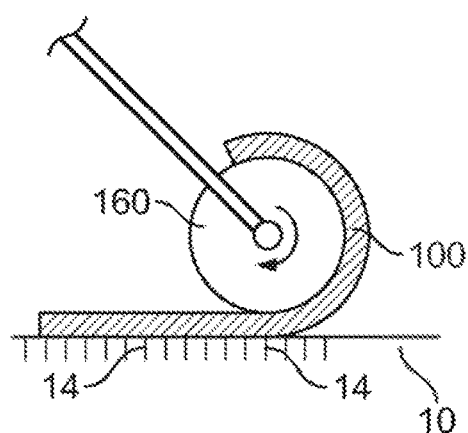
FIGS. 7C and 7D illustrate various mechanisms for application of a dressing.
Figure 7D:
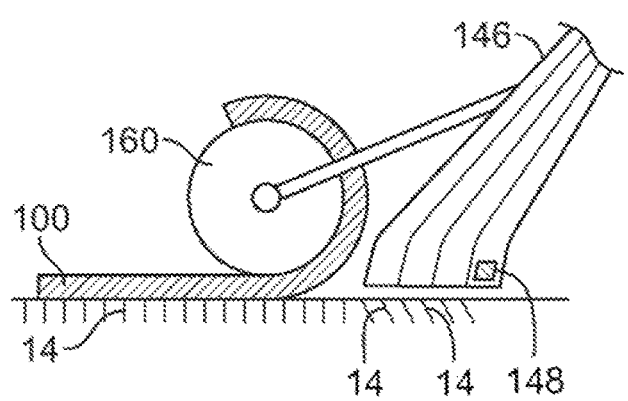

FIGS. 7C and 7D illustrate another mechanism for application of a dressing 100. As shown, a dressing 100 can be applied using a roller applicator 160. The roller applicator 160 can strain the dressing 100 as it applies the dressing 100 to tissue 10 over the lesions 14. Alternatively, the roller applicator 160 can apply a pre-strained dressing 100 that compresses tissue 10 and the lesions 14 upon positioning on the tissue 10. FIG. 7D illustrates a roller applicator 160 that is coupled to a lesion creating device 146, which creates the lesion 14 and where movement of the device 146 causes the roller 160 to apply the dressing 100. The device 146 can also include one or more sensors 148 to provide feedback of location to the system or can be used to detect movement of the device 146. In some variations, the roller applicator 160 may comprise a ribbon spring (or other spring mechanism or tension control mechanism) to resist rotation of the roller until a specific tension threshold is achieved.

Figure 8A:
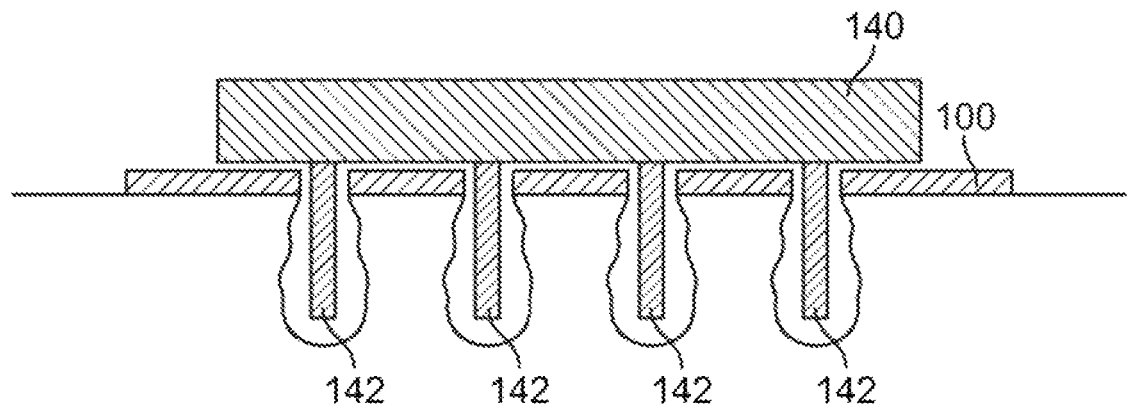
FIGS. 8A and 8B show a dressing positioned adjacent to treatment devices that are used to create lesions within tissue.

FIG. 8A shows another application of a dressing 100 as described herein. In this variation, the dressing 100 is coupled to a treatment device 140. The treatment device 140 can create a lesion through any variety of treatment modes where the active elements 142 of the treatment members pass through openings in the dressing. For example, the treatment device 140 can create the therapeutic lesion using RF energy, plasma, cryogenic energy, microwave energy, laser, optical energy (non-laser) chemical, resistive heat, ultrasound energy, or via mechanical energy. As shown, a dressing 100 can be coupled to the treatment device 140 so that after creation of the lesions, the treatment device 140 can be removed leaving the dressing in place to apply compression to the lesions. Alternatively, the treatment device 140 can be directly applied over a dressing 100 that was previously positioned. In some variations, the dressing 100 may comprise a pattern of treatment openings with predetermined size, spacing or location, and the treatment device 140 may comprise a matched pattern or array of treatment elements 142 with the same spacing or location. In some variations, the pattern of treatment openings in the dressing 100 may comprise a repeating sub-pattern, and the treatment device 140 may comprise a matched pattern or array of treatment elements 142 to the dressing subpattern of openings. In these variations, the dressing 100 may comprise indicia to delineate the locations of the subpatterns. Thus, the treatment device 140 may be used at multiple regions of the dressing 100. The pattern or array of treatment elements 142 of the device 140 may comprise at least 2, 3, 4, 5, 6, 7, 8, 9, 10, 15, or 20 treatment elements.

Figure 8B:
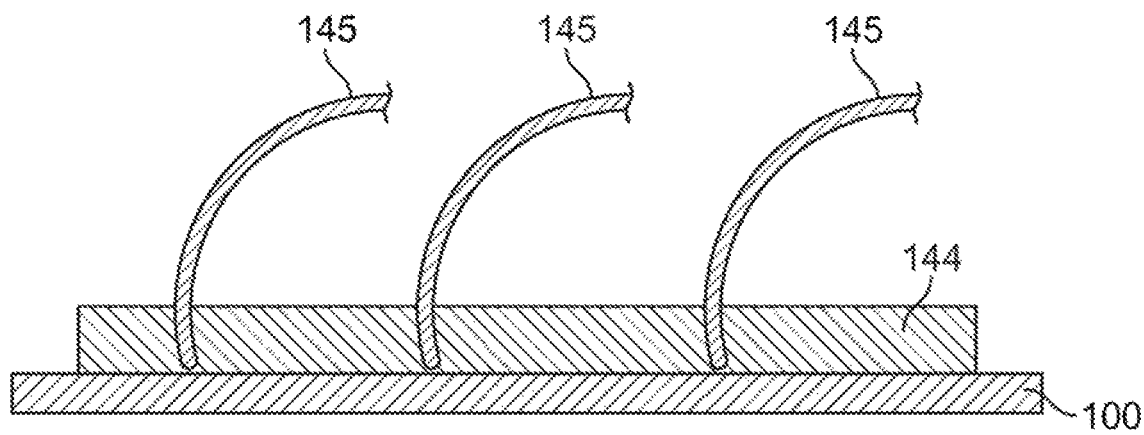

FIG. 8B illustrates another variation of a dressing 100 in combination with a treatment device 144. In this variation, the treatment device 144 creates openings within the dressing 100 before or during the actual treatment. For example, the treatment device can employ a laser, optical/light, chemical, ultrasound or electrical energy to create an opening through the dressing while creating the therapeutic lesion in tissue beneath the dressing. Moreover, device 144 can apply energy to a dressing 100 to activate the dressing 100 induce or adjust strain. In such a case, the dressing can be in an unstrained condition prior to activation by the device 144. Alternatively, or in combination, the device 144 can reduce or increase a strain in the dressing depending upon the desired application. FIG. 8B illustrates lesion creating elements 145 positioned adjacent to the dressing 100. In the event that the device 144 employs a laser to create lesions, the laser is emitted from the elements 145 and can either pass through the dressing 100 or can create openings in the dressing. In those variations where the lesion creating elements 145 comprise electrodes or mechanical members, the elements 145 can pass through the dressing when advanced from the device 144.

Figure 9A:
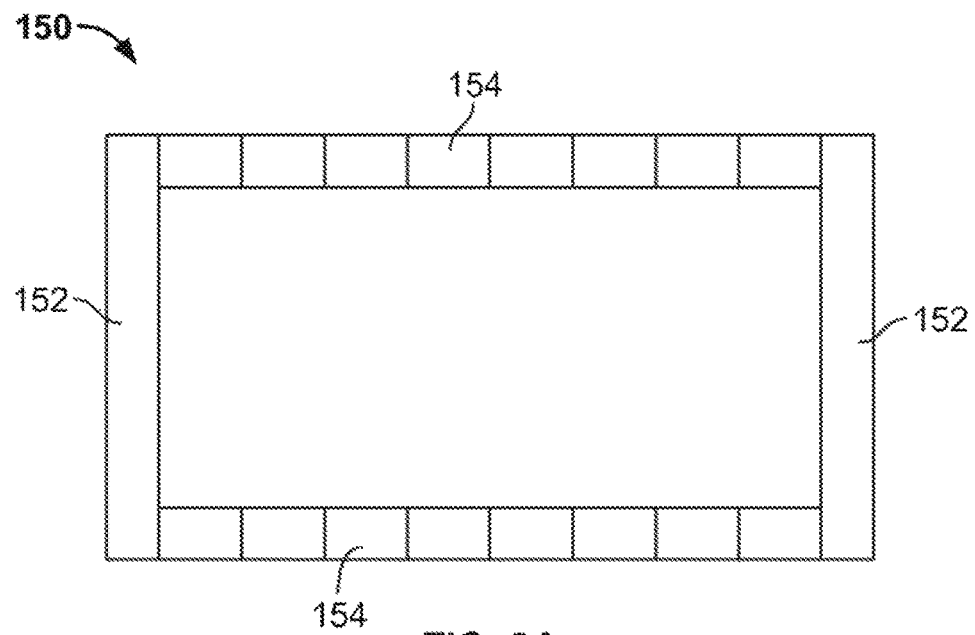
FIGS. 9A and 9B show an adjustable frame that permits shaping of the frame to adjust to a contour of a surface of tissue.
Figure 9B:
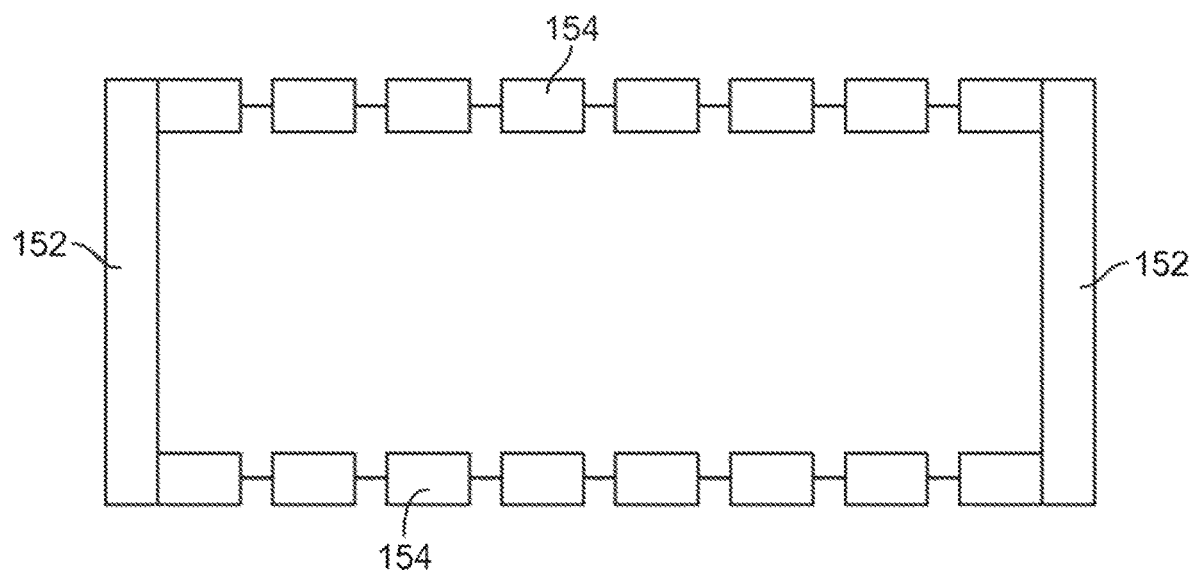

In many cases, the dressings described herein are intended for positioning on contoured tissue surfaces rather than planar surface. Accordingly, there may be a need to provide a dressing that can approximate the contoured shape prior to affixing to the tissue surface. FIGS. 9A and 9B show one possible solution to adjust a contour of a dressing described herein. FIG. 9A shows a variation of an adjustable frame 150. In this example, the frame 150 includes a plurality of adjustable links 154 coupled between two end-pieces 152. However, variations of the frame 150 include adjustable links 154 forming the entire periphery of the frame. As discussed above, the frame 150 can include one or more fixtures to permit retention of the dressing. FIG. 9B illustrates the adjustable frame 150 where one or more of the plurality of links 154 can be adjusted or extended to permit a portion or all of the frame 150 to form a contoured shape. Although not illustrated, a dressing attached to the frame 150 will then be in a better configuration when being secured to a contoured tissue surface.

In additional variations, a frame can be used without a dressing to apply strain to the tissue in a similar manner as a dressing. For example, a deformable frame can apply a compression force to the tissue and then can be affixed to the tissue in a manner as described herein (e.g., adhesive, mechanical fasteners, sutures, etc.) Doing so allows the frame itself to compress tissue to assist healing of the treated region.

Figure 9C:
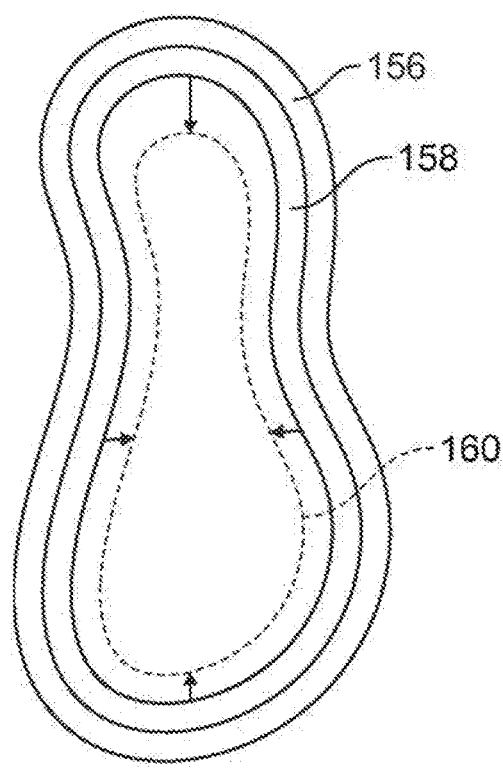
FIG. 9C shows a variation of a frame employing an expandable member or bladder to compress tissue within the perimeter of the bladder.

FIG. 9C shows another variation of a frame 156. In this variation, the frame 156 employs an expandable member or bladder 158. When affixed to tissue the bladder can be inflated or expanded to position 160 to provide compression within the area bounded by the frame 156 and bladder 158. In other variations, a foam (open cell or closed cell) may be provide within the bladder to maintain the bladder in an expanded state, and negative pressure may be applied to reduce the bladder/foam size. In still other variations, the frame may comprise a foam member in lieu of a bladder member to provide a resilient or contouring surface or structure for the frame.

Figure 9D:
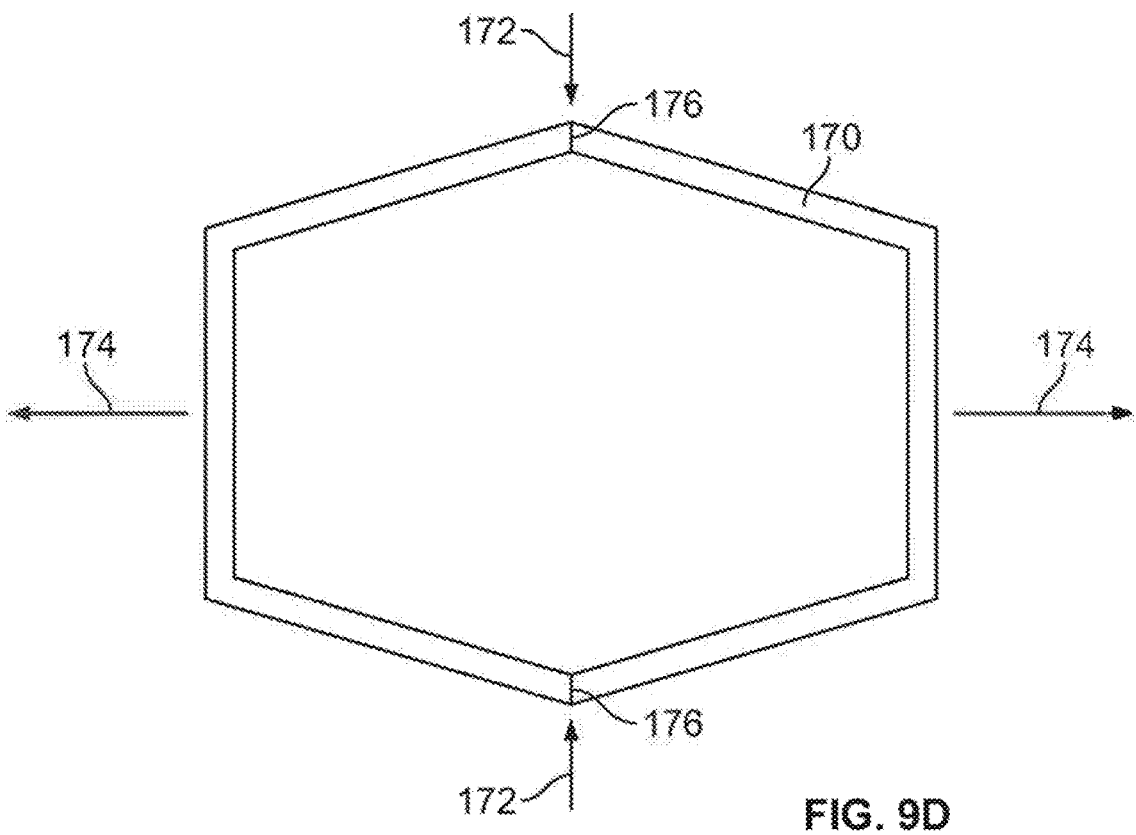
FIG. 9D illustrates another example of an adjustable frame that is used to compress tissue or expand a dressing.

FIG. 9D illustrates another example of an adjustable frame that is used to compress tissue. In this example, the frame 170 can have hinges or joints 176 that transmit a force 172 applied at the joints to result in an expansion force 174 at the edges of the frame. In some variations, the frame is biased to return to its initial shape upon application of a force. In such a case, after force 172 is applied to the frame, the frame 170 provides compression within the area bounded by the perimeter of the frame 170. In use, a physician could apply the activation force 172 to the frame, then adhere portions of the frame 170 to tissue. As the frame 170 attempts to return to its initial shape, the return force compresses tissue within the frame. In an alternate variation, the frame 170 is not biased. Instead, the frame 170 can be affixed to an elastic dressing (not shown) as described above. In this example, application of force 172 causes expansion or straining of the elastic dressing in direction 174. A physician or medical practitioner can then affix the strained dressing 170 to tissue where the resiliency of the tissue compresses the tissue.

The dressings of the present invention can also provide temporary results to simulate a clinical effect. These temporary results can allow a patient or physician to determine the type or amount of treatment desired. For example, a physician can position pre-strained dressings on a patient to show the patient the results of a procedure given a predetermined amount of shrinkage or lift. Such a feature allows a physician to position dressings having a predetermined amount of strain on a patient so that the patient can visually see the results of the given reduction. For example, a physician can position dressings that lift the skin by a given amount so that the patient can determine whether more or less lift is desired. The goal is to simulate clinical results and allow a patient to see a real time simulated clinical result via the application of the dressings. Such pre-strained dressings can be provided as a kit having varying ranges of displacement with corresponding templates to assist the physician in applying apply therapeutic treatments to match the temporary state of the tissue. In this way, a patient can observe the simulated clinical result, once a desired result is achieved; the physician can select treatment templates based on the dressings that are used to produce the temporary effect. Use of the dressings to simulate a clinical effect can be used in any number of cosmetic procedures outside of skin tightening. In additional variations, the simulated clinical effect can be used to establish a treatment plan. Such a treatment plan can include the amount of or location where the therapeutic treatment. The simulated clinical effect can be processed through a computer analysis to provide the physician with a treatment plan based on the type of dressing used or amount of lift used to produce acceptable or desired results.

Figure 10A:
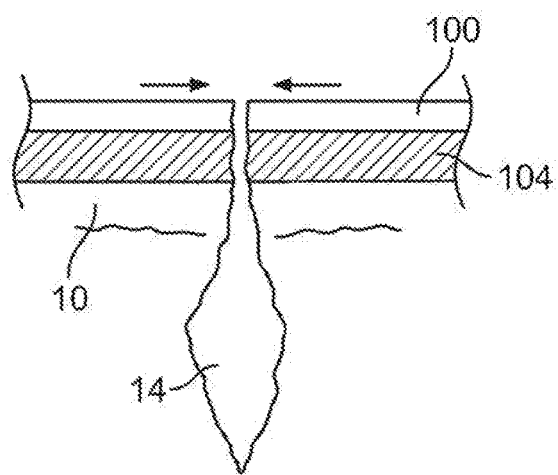
FIGS. 10A to 10C illustrate a settable adhesive for use with dressings of the present disclosure.
Figure 10B:
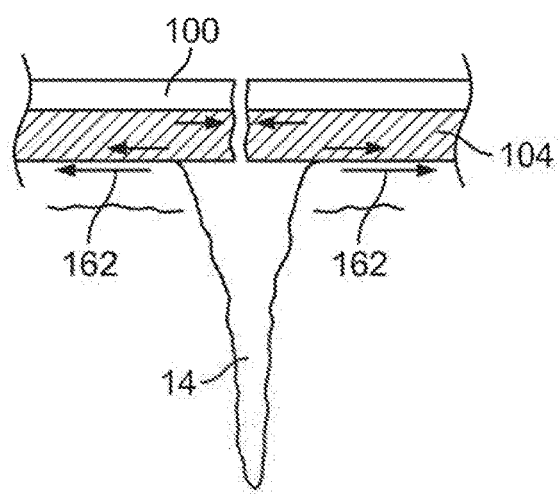
Figure 10C:
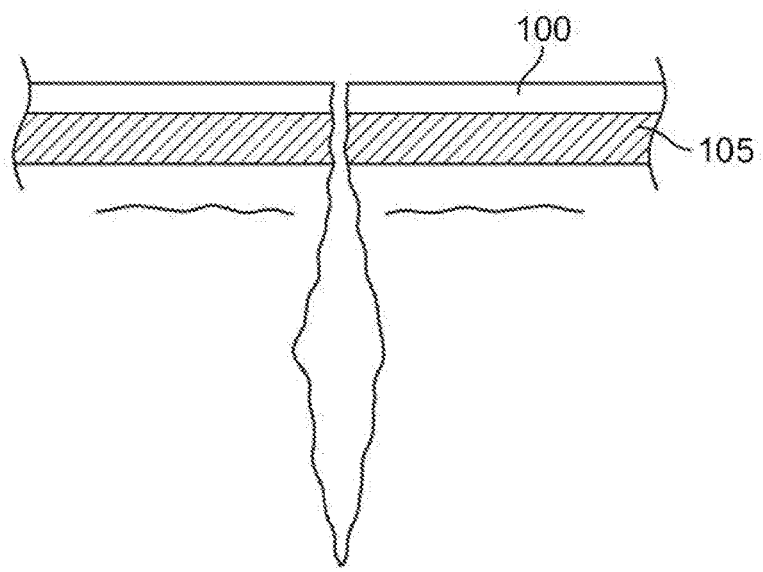

FIGS. 10A to 10C illustrate another aspect for use with dressings of the present invention. As shown in FIG. 10A, a dressing 100 that is placed over a lesion 14 when used to apply compression to the dermal layer 10 of skin. In this variation, the dressing 100 includes an adhesive layer 104. In some variations, the adhesive layer 104 is sufficient to prevent creeping or movement of the tissue 10 subsequent to placement of the dressing 100. However, in certain circumstances, as shown in FIG. 10B, the tissue 10 contacting the adhesive layer 104 can begin to creep causing the lesion to move in the direction shown by arrows 162 resulting in opening of the lesion 14. The creep of the tissue 10 can occur due to the restoring force of the skin, which may be higher in a particular target location. Alternatively, creeping of tissue can occur due to the thickness of the elastic layer or when the adhesive layer is non-rigid and/or deformable and takes time to secure the dressing to the tissue.

FIG. 10C provides a representation of an alternate variation of a dressing 100 having an adhesive material 105 that can be activated or set. In some variations the settable adhesive material 105 is set from a liquid or viscous phase to a solid phase via UV or IR irradiation or even oxidative curing. In some variations, use of oxidative curing allows for securing of the dressing without heating of the tissue and/or dressing. As shown in FIG. 10C, the adhesive material 105 solidifies to keep the lesion closed but also remains pliable to allow the dressing 100 to remain pliable and conform to the curvature of the tissue.

In additional variations a dressing can be used to limit the lesion size or to minimize collateral damage to tissue. For example, a solid dressing can be applied to tissue as described above. Next, a laser can then be used to create openings in the dressing as well as to create the lesion. For instance, an Er:YAG laser or an Er:YsGG may be used with a Cr2+:or CR2t:ZnSe Q-switching device, or a Cr2+:Cr2t:ZnS Q-switching device to apply a pulse in a Q switched mode followed by a free running mode or normal mode. The pulse could be used to remove a portion of the dressing since the pulse produces a plasma initiation and expansion to photomechanically remove the layer of the dressing (e.g., a silicone layer). The free running mode operation creates a micro lesion via photothermal ablation of the tissue.

Figure 11A:
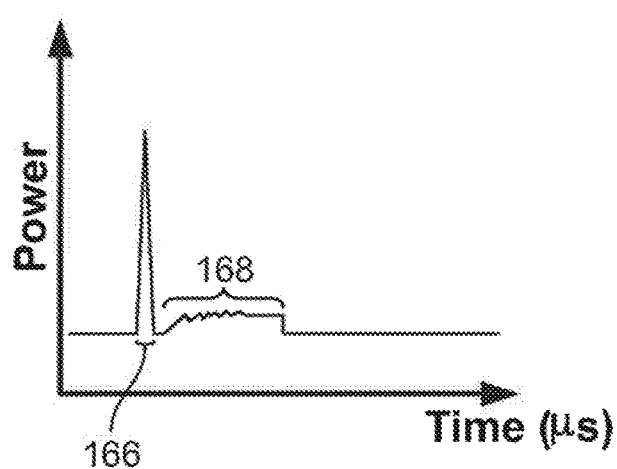
FIG. 11A illustrates an exemplary plot of power versus time for a laser treatment application so that a single laser can create an opening in a dressing and a subsequent lesion at the site of the opening.

FIG. 11A illustrates an exemplary plot of power versus time for a laser treatment application so that a single laser can create an opening in a dressing and a subsequent lesion at the site of the opening. As shown, the first applied pulse 166 reaches a power level much greater than that of the subsequent free running mode pulse 168. One benefit of creating openings in the dressing simultaneously or immediately prior to creating the lesions is to eliminate alignment of the openings and lesions.

Figure 11B:
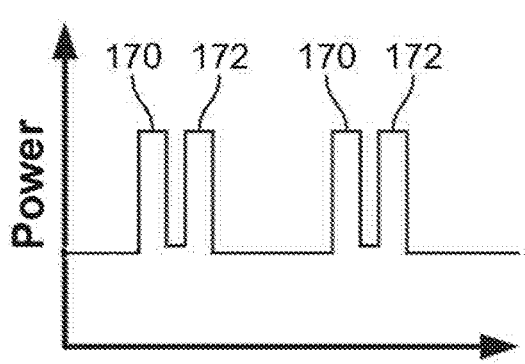
FIGS. 11B to 11E illustrate another variation of using multiple laser sources to create lesions in solid dressing.
Figure 11C:
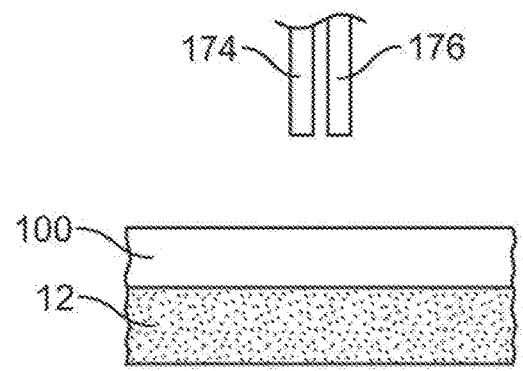

FIGS. 11B and 11C illustrate another variation of using a solid dressing and creating openings in the dressing once the dressing contacts the tissue. As illustrated in FIG. 11C, the treatment can include two ore more different types of lasers 174, 176, where one of the lasers 174 can be selected such that it is highly absorbed by the dressing 10. While the second laser 176 can be selected such that it is highly absorbed in tissue. For example, a CO2 and Er:YAG laser can be used together. The wavelength of the CO2 laser is highly absorbed by silicone and the wavelength of the Er:YAG laser is highly absorbed in skin. In one example, the wavelength required to create openings in the dressing is 10.6 μm while the wavelength for creating lesions could range from 1.9 to 3.3 μm. The lasers can be arranged so that they are either co-axial or confocal (e.g., the laser elements if FIG. 11C can be rotated or moved so that each laser targets the same region.) Alternatively, the lasers can be configured to deliver light in a concentric manner. In use, the lasers are time-delayed as shown in FIG. 11B, which illustrates a graph of power versus time. As shown, the first laser 174 delivers a first pulse 170 to create the opening in the dressing 10. The pulse 172 from the second laser 176 can be staggered or delayed to allow for ejection and/or removal of debris. While any variation of lasers can be used in this configuration, one desirable variation can include the use of two low power lasers to provide each source of light. Alternatively, a more complicated dual wavelength system can be used. Such a system could deliver multiple wavelengths of light as described above.

Figure 11D:
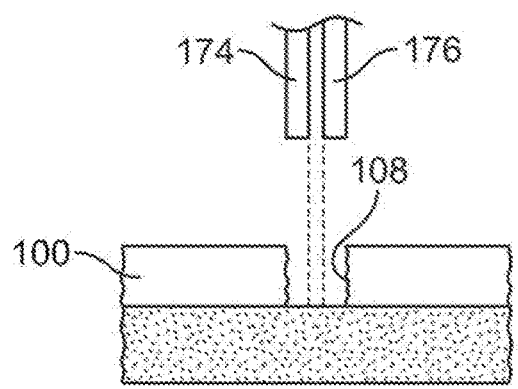
Figure 11E:
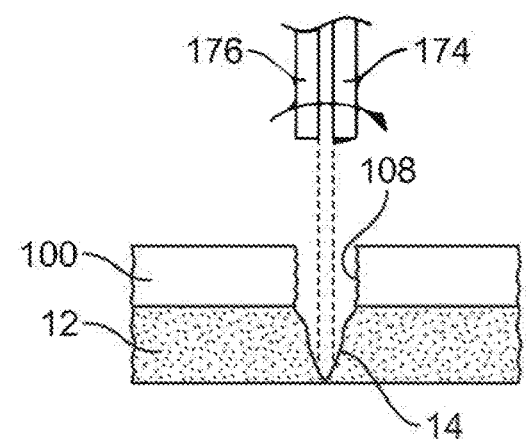

FIG. 11D shows the system of FIG. 11C, where the first laser 174 creates an opening 108 in the dressing 100 but not the skin since the laser is not absorbed by the skin. FIG. 11E shows the second laser 174 creating the lesion 14 through the previously created opening 14.

The above system or configuration allows for a skin tightening therapy with an adhesive patch applied to skin with the skin and patch ablated in situ. The patch is applied to untreated skin under tension with an adhesive. The patch initially does not have holes over the areas where lesions are to be formed. The entire patch may be solid or may have holes or other features to position and/or stretch the patch. An initial laser beam ablates holes or other features in the patch to expose certain areas of the skin. The exposed areas can then be treated through holes in the patch. The laser parameters are such that the patch material is cleanly ablated with a minimum of thermal damage to the underlying skin. A second laser beam of possibly different character is then used to ablate a controlled amount of skin. An additional benefit of creating openings in the dressing and subsequently creating lesions is that the lesion pattern and/or openings in the dressing can be customized during a procedure rather than needing to follow the pattern of a pre-configured dressing.

One benefit of creating openings in the dressing in situ is that there is no need for orienting a dressing having pre-made openings with previously created lesions. Yet another benefit of creating openings in-situ is that the pattern or features of the holes in the dressing are customized to match the lesions.

Figure 12A:
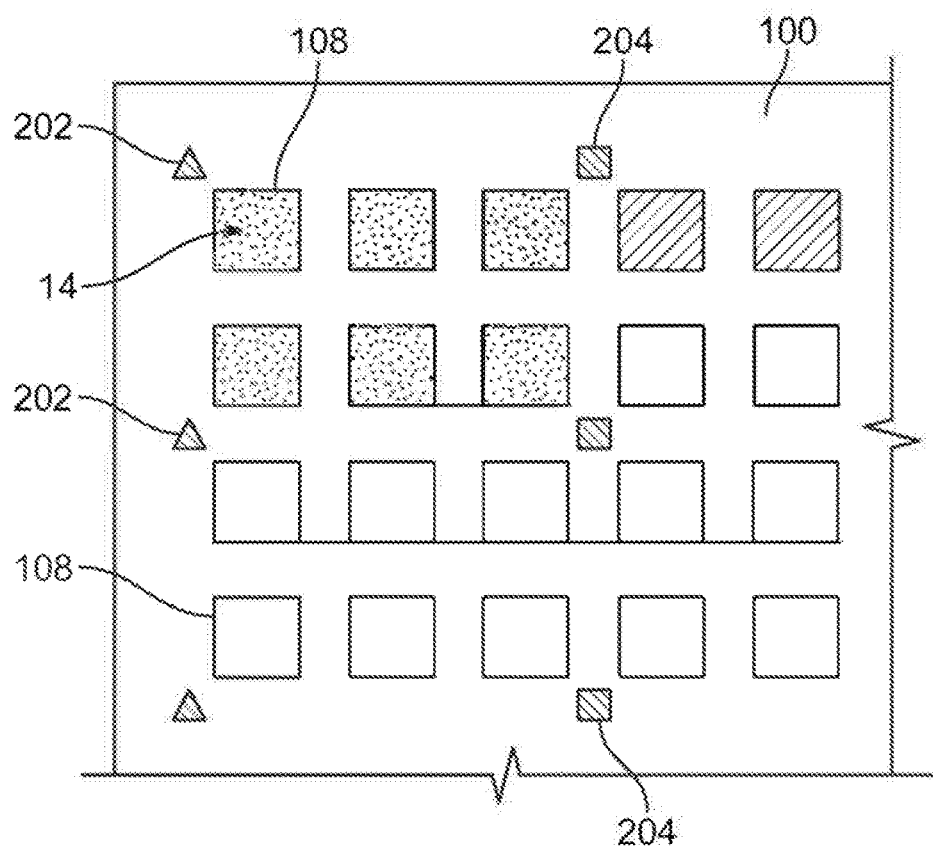
FIGS. 12A and 12B shows an example of a dressing having registration features that allow for detection by the treatment device.

FIG. 12A shows an example of a dressing 100 having one or more registration features 202, 204 allowing for detection and/or recognition regarding characteristics of the dressing. For example, FIG. 12A shows registration features 202 and 204, which allow for optical scanning or reflecting light that can be used to confirm alignment of the treatment device. Alternatively, or in combination, the presence or relative position of the registration features 202 and 204 can provide any range of information regarding the pattern of openings 108 or even the location where treatment should occur. For example, in FIG. 12A, lesions are created in the openings that are within specific registration features 202 and 204.

Once the system obtains feedback regarding the registration features, the system can confirm that the treatment device is in the correct position. Subsequently, image analysis hardware and software can be used to recognize the patterns or openings 108 in the dressing 100 to either control the treatment parameters, to maintain a database of treatment areas, or to perform some other custom treatment depending upon type of dressing or orientation of the dressing.

One approach is to position a handheld scanning handpiece directed at the approximate location of the treatment. The system can determine whether positioning of the handpiece is within an acceptable tolerance using an optical detection of one or more registration features 202, 204. Once the system confirms correct or acceptable positioning, the system can then permit or trigger a treatment cycle. For example, a laser scan pattern can be released on a time scale sufficiently rapid enough (<50 msec) such that inadvertent motion of the handheld scanning handpiece does not appreciably affect the pattern. The handheld scanning handpiece can be repositioned to treat the next zone, and the optical detection of registration features at the correction positioning of the dressing with respect to the handpiece will again trigger the release of a laser scan pattern.

Alternatively, a handpiece with either scanning patterns or fixed patterns (including a single shot) can be manually positioned laterally to the dressing, with optical detection of the registration features 202, 204 triggering individual firing events. One example involves the use of an optical mouse-type arrangement in which a light source such as an LED projects onto the dressing surface and the reflected or scattered light from the dressing is re-imaged into an optical detector as the handheld device is manually moved laterally across the dressing.

Alternatively, a complete image may be acquired by an imaging system, and image-processing software may be used to create a custom scan pattern to be delivered. The positioning of the dressing with respect to the laser delivery system, the particular configuration of the dressing, the desired pattern of lesions may all be processed to determine a customized laser scanning pattern appropriate for a particular dressing and patient. In this realization, a relatively large area may be treated by a scanned laser pattern, which may require a duration that is long enough that movements of the patient with respect to the laser delivery device may occur. The invention may interrupt delivery of laser pulses is motion of the registration features 202, 204 is detected. The positioning may be restored and laser firing resumed. Alternatively, a new image may be acquired and a new laser delivery pattern computed and delivered.

Figure 12B:
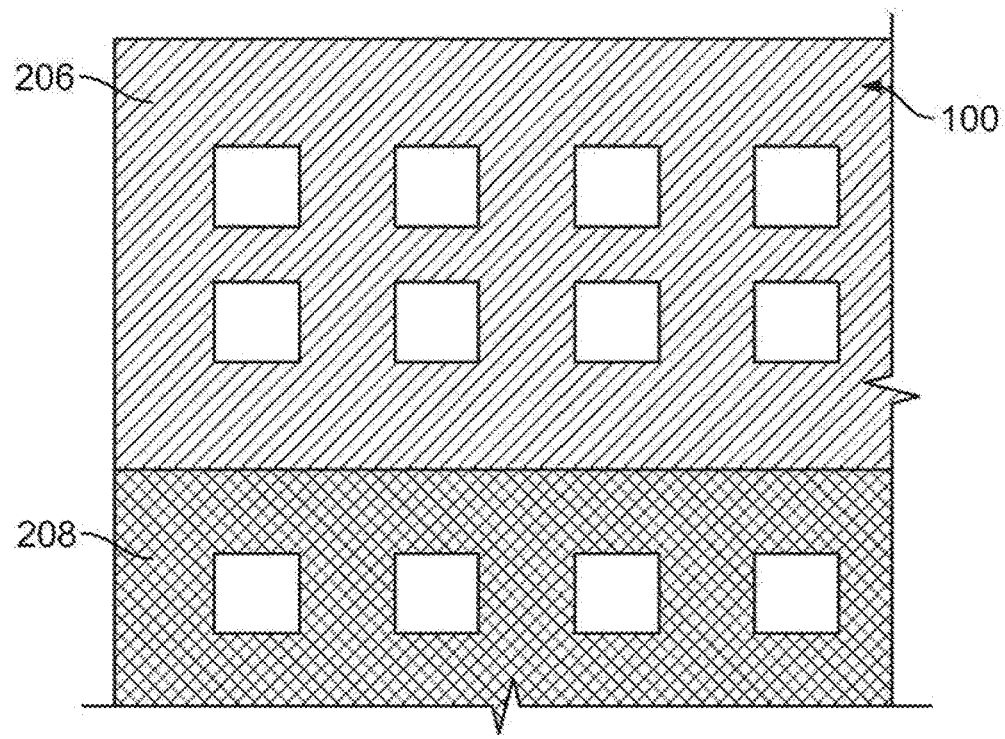

FIG. 12B provides a partial illustration of another variation of a dressing 100. In this variation, a dressing 100 can include a surface that provides a particular optical or other identifiable property that can be recognized by the treatment device to alter treatment parameters or lesion location based upon pre-determined parameters. For example, the dressing 100 can include a particular, reflective, absorptive, or scattering characteristic that is recognized by the treatment device. In addition, as shown, a dressing can include a first region 206 having a first set of characteristics, and a second region 208 having a second set of characteristics.

Figure 13A:
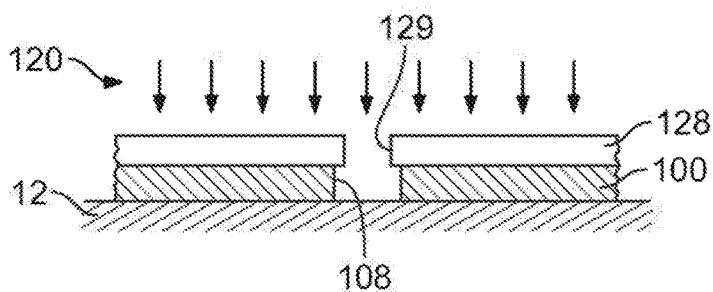
FIGS. 13A to 13E show another variation of a dressing covered by a mask that directs laser energy to openings within the dressing to control placement of lesions.
Figure 13B:
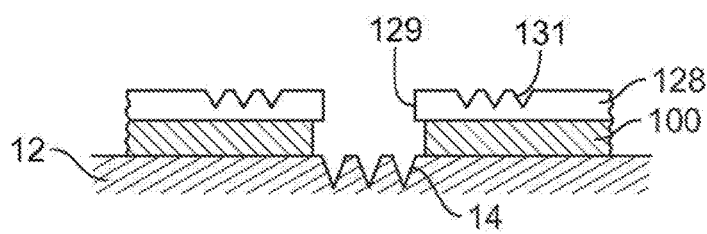
Figure 13C:
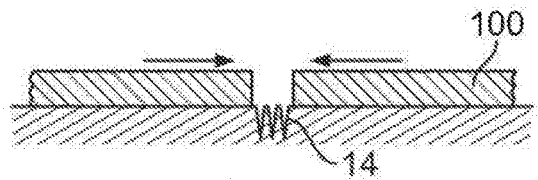
Figure 13D:
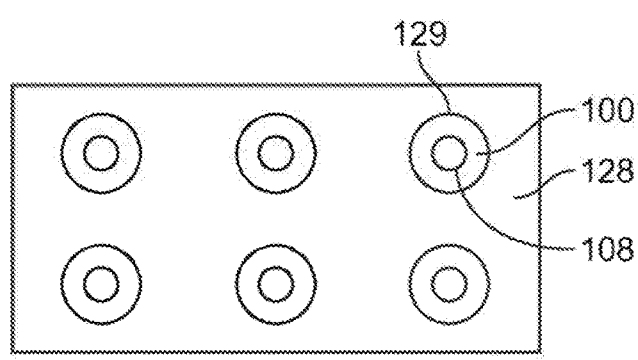
Figure 13E:
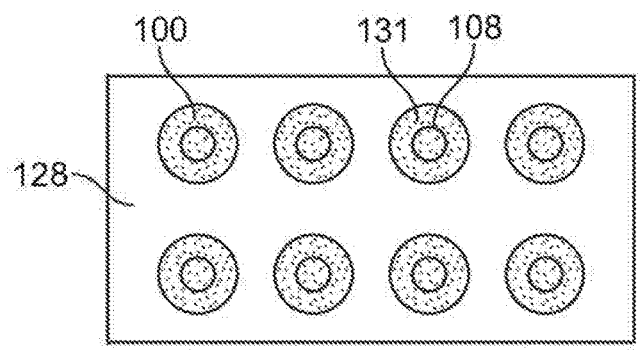

FIGS. 13A to 13E show another variation of a dressing 100 covered by a mask 128 where the dressing 100 and mask 128 allow for a treatment device to create lesions at specific areas, thereby eliminating the need to align the dressing with the lesion. As shown, the mask 128 can include openings 129 that are in alignment with opening 108 in the dressing. Optionally, the mask 128 can apply strain to the dressing 100. FIG. 13A illustrates the dressing 100 in a strained configuration to place the tissue 12 in a state of traction. The dressing 100 and mask 128 are exposed to the treatment energy 120 (e.g, a laser or other treatment modality). The therapeutic energy 120 creates ablation patterns 14 and 131 in the tissue 12 and the mask 128 respectively. FIG. 13C shows removal of the mask 128 and eventual compression/closure of the lesions 14 as the dressing 100 contracts. FIGS. 13D and 13E illustrate top planer view of a dressing 100 and mask 128 having respective openings 108 and 129. FIG. 13D shows the dressing 100 and mask 128 pre-treatment. FIG. 13E shows the dressing 100 and mask 128 after the ablation process. As shown, the ablation pattern 14 and 131 can be created over a wider area than the opening 14 in the dressing 108 but only forms lesions 14 in the tissue in a limited manner at the exposed areas.

Figure 15A:
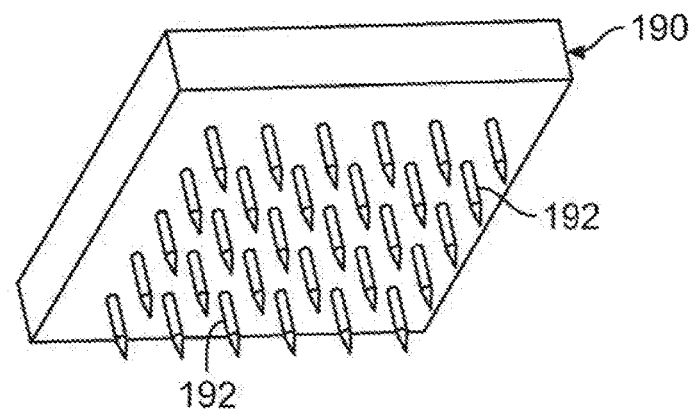
FIGS. 15A to 15D illustrate another use for dressings of the present disclosure.
Figure 15B:
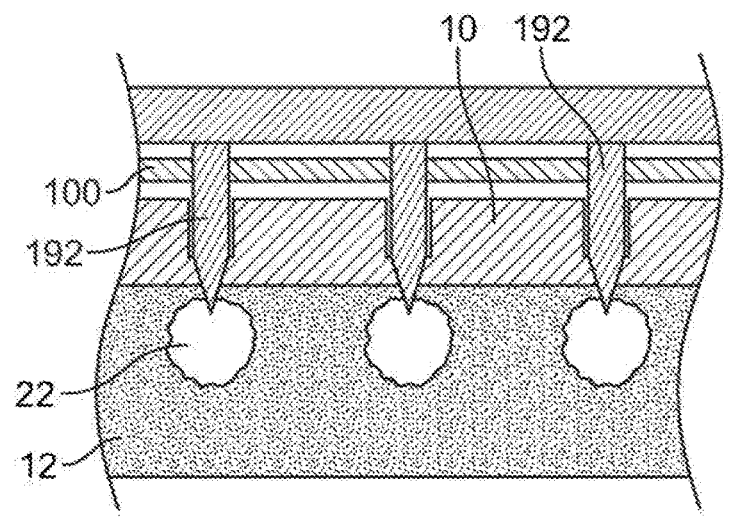
Figure 15C:
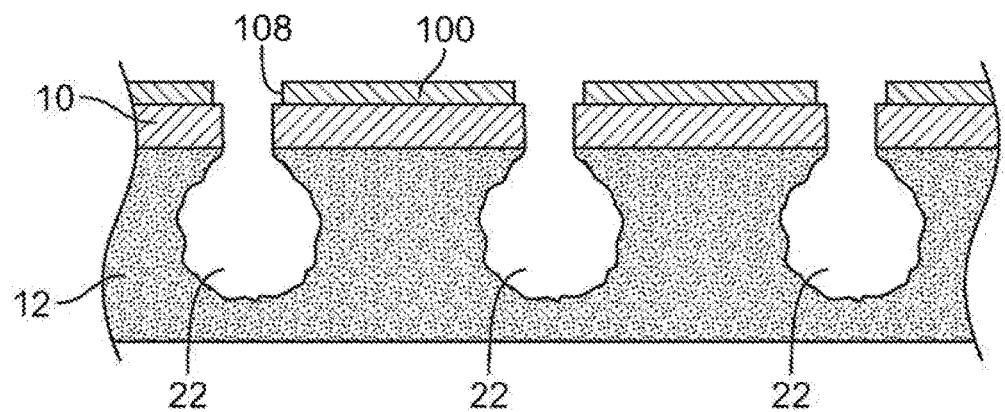
Figure 15D:
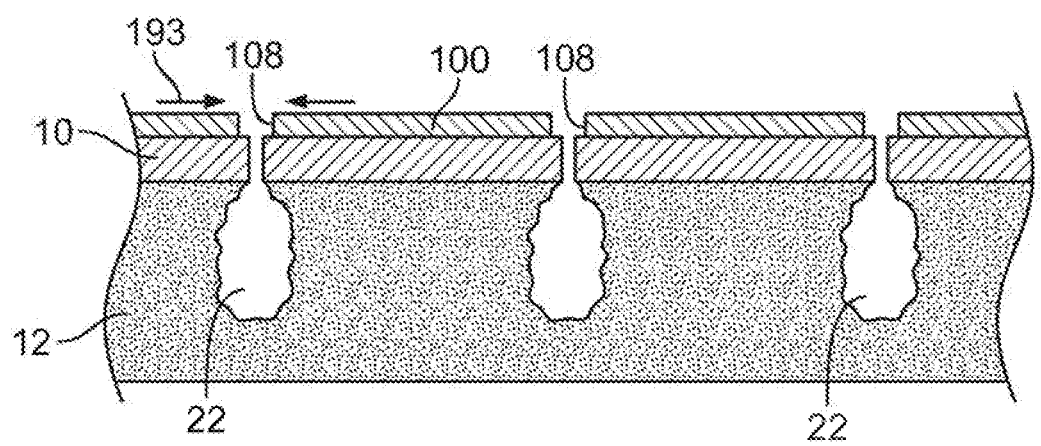

FIG. 14A illustrates another advantage of creating a lesion 14 in situ with the dressing 100. As shown in FIG. 14A, the lesion 14 as well as the opening 108 in the dressing 100 can be made to have a unique shape that can be made or modified during the procedure. For example, FIG. 14A shows a dressing 100 with a lesion 14 in tissue, where both the lesion 14 and opening 108 are made to have a longer dimension when viewed along 14C-14C (as shown in FIG. 14C), when compared to direction 14-B-14B (and as shown in FIG. 14D). Furthermore, the lesion pattern can be a non-linear design. An additional example of such patterns is shown in FIG. 14D FIGS. 15A to 15D illustrate another use for dressings of the present disclosure. FIG. 15A illustrates an array 190 of electrodes 192 adapted to penetrate subdermal tissue, such as subcutaneous layers 12. FIG. 15B illustrates a dressing 100 as described herein, where the dressing is strained and placed over the electrodes 192 as shown in FIG. 15B. The electrodes 192 (e.g., RF electrodes or any other energy modality described herein) applies energy to the subcutaneous fat layer 12 to lyse, burn, or otherwise breakdown the fat to create a lesion 22 or cavity 22. FIG. 15C illustrates removal of the electrode array 190 leaving the dressing 100 in place against the dermal region 10 of tissue. Because the dressing 100 is in a strained configuration, removal of the dressing 100 from the electrode array causes movement of the dressing 100 to close the openings 108 as described above.

Figure 16:
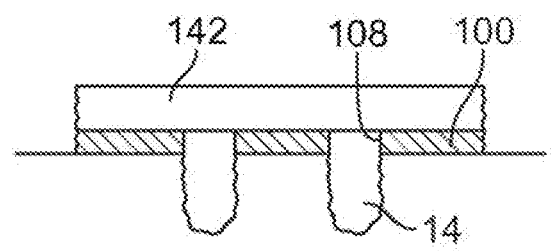
FIG. 16 depicts an additional use of a dressing as a mask to direct creation of a lesion.

FIG. 16 depicts an additional use of a dressing 100 as a mask to direct creation of the lesion 14. As illustrated, an electrode 142 or other lesion creation element is placed against a dressing 100 such that activation of the element 142 creates lesions 14 through openings 108 in the dressing 100. As discussed above, creating lesions 14 through openings 108 in the dressing 100 eliminates the need to match openings in the dressing to lesions. The use of the dressing 100 as a mask type element eliminates the need for electrodes penetrating into tissue.

Elastomeric dressings of the present disclosure can also be used by affixing to the tissue, stretching or straining once placed on tissue. Then creating the lesions in the tissue. The dressing can then be released to compress the lesion. The dressing can also be removed so that the natural elasticity of the skin or tissue helps appose the lesion openings. Accordingly, the dressing can be removed.

In additional variations, the dressings or frames described herein can be affixed to external structures placed on a patient to provide the degree of lift or tissue movement required for an acceptable clinical effect. For example, a cap or similar structure can be placed on a patient's head and serve an anchoring type device that allows the dressings or frames to displace tissue for an acceptable simulated visual result.

The devices, methods and kits described herein can be used for applying force to any portion of tissue to compress, reposition, or lift tissue as required by the intended cosmetic application (e.g., lifting of the breast, stretching scalp tissue to increase a density of implanted, underarm, abdominal procedures, etc. The dressing described herein can be fabricated from any biocompatible material that can provide the compressive force necessary to achieve the intended result. For example, the dressings can comprise a polymer, a shape memory polymer (e.g., acrylatebased, styrene-based and epoxy-based shape memory polymers), or biocompatible polymer (e.g., silicone). The dressings and/or frame can be transparent or opaque or have other features as required by the intended application. The strain rates of the dressings and frames described herein can range from 1% to 100% either uni-directional, uni-axial, or bi-axial.

The fixation means described above can include any conventionally known means to secure similar dressings or frames to tissue. For example, the devices can be secured to tissue in a variety of ways (either temporarily affixed or affixed until the fixation means is removed). For example, the devices can be removably secured to the tissue with an adhesive, with a skin piercing device, or the like. Suitable adhesives include pressure sensitive adhesives, such as polyacrylatebased, polyisobutylene-based, temperature activated adhesives, chemically activated adhesives and silicone-based pressure sensitive adhesives. Suitable skin-piercing devices include clamps, needles, microneedles, sutures, anchors, staples, microtines and the like.

The devices may have any suitable or desirable shape or size. In some examples, the shape of the dressings or frames can be adjusted before, during or after the procedure. For example, the devices may have a shape selected from the group consisting of rectangles, circles, squares, trapezoids, toroids, ovals, or segments and combinations thereof. For example, some devices may be substantially circular, others may be substantially toroidal, and still others may be substantially rectangular.

Figure 17A:
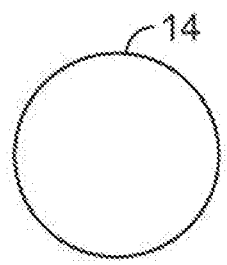
FIGS. 17A and 17B provides a top view to demonstrate compression or application of force to a lesion.
Figure 17B:
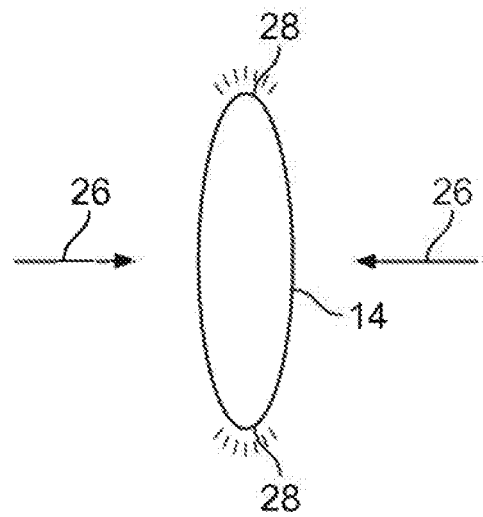
Figure 18A:
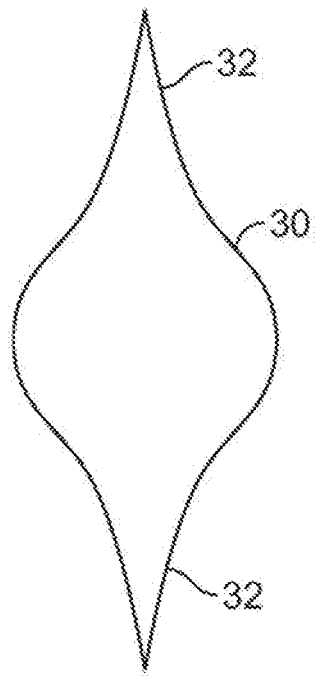
FIGS. 18A to 18F show variations of shaped lesions having geometries to prevent high stress areas when compressed.
Figure 18B:
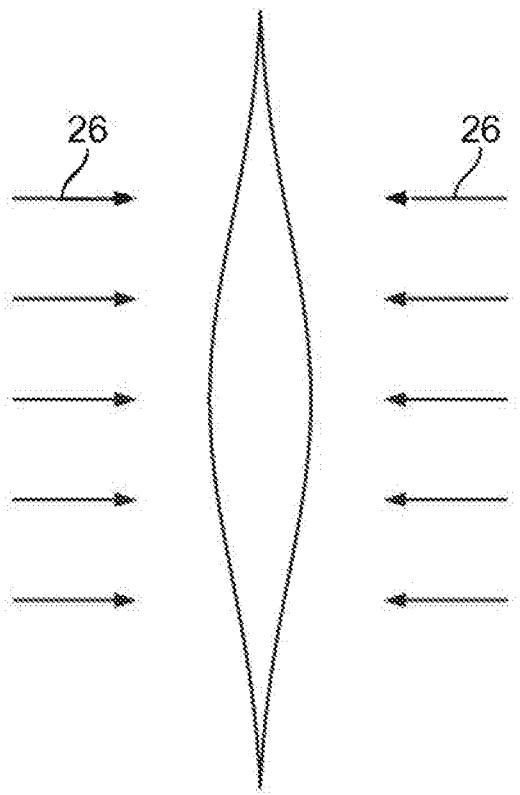
Figure 18C:
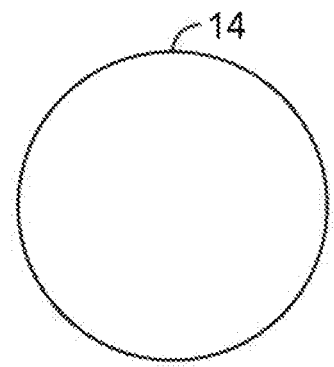
Figure 18D:
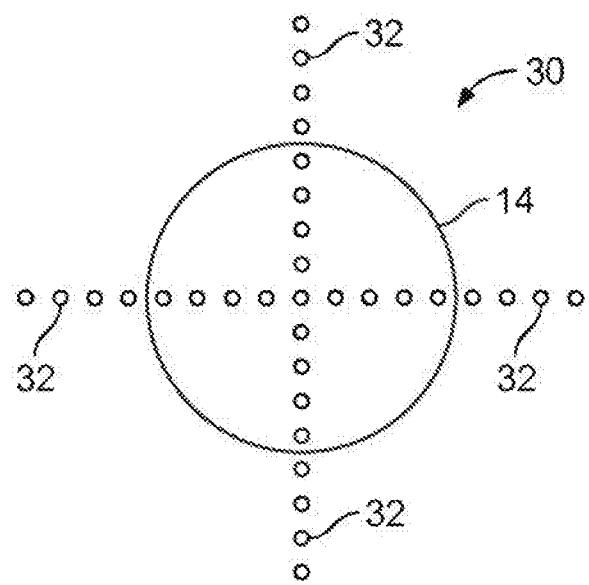

In another aspect, altering the geometry of a lesion to assist in wound healing can be combined with methods and devices described herein to improve the outcome of a treatment. For example, FIG. 17A provides a representative illustration of a top view of a lesion 14 without application of any compressive force. FIG. 17B illustrates the lesion 14 of FIG. 17A, where a compressive force, as described above and illustrated by arrows 26, attempts to close the lesion 14. However, the lesions 14 circular geometry creates regions of increased stress 28. The high stress regions 28 are not desirable for a number of reasons. For example, the high stress regions 28 can impede the healing process. Moreover, the high stress regions 28 caused increased resistance when attempting to close the lesion 14. For example, the high stress regions 28 can provide an opposing force to the dressing and ultimately render the procedure less effective. FIG. 18A shows a variation of a shaped lesion 30 intended to reduce areas of high stress when the lesion 30 is compressed as discussed herein. The lesion 30 can be created via a single treatment or can comprise a number of treatments to produce a desired shape. For example, in FIG. 18A the lesion 30 can be created to be asymmetrical so that portions 32 of the lesion 30 do not generate high areas of stress when the lesion is compressed (see e.g., FIG. 18B). In one example, a shaped lesion 30 is created via a slit in tissue and superimposing a circular lesion on the slit portion. Alternatively, as shown in FIG. 18C, a standard lesion 14 is created and then a secondary process creates one or more additional lesions 32 to create a shaped lesion 30 as shown in FIG. 18D. The creation of the base lesion 14 can be made by any conventional means (e.g. a $CO_2$ laser) that creates a lesion of the desired size. The additional lesions 32 can be created using a means that allows creation of smaller lesions.

Figure 18E:
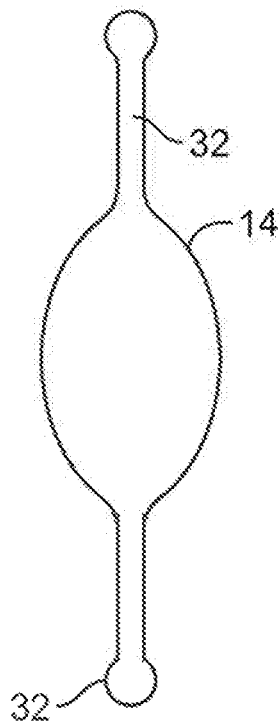
Figure 18F:
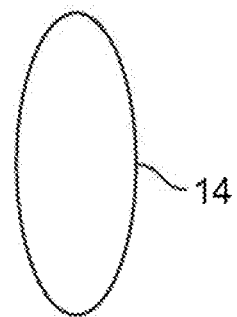

FIG. 18E illustrates another variation of a lesion 14 with features 32 to prevent high stress areas upon compression of the tissue. Such complex lesions can be created using a masking approach or creating series of therapeutic treatment lesions similar to that shown in FIG. 18D. FIG. 18F illustrates another lesion geometry conducive to avoiding high stress areas upon compression of tissue. In this variation, the lesion 14 includes a relatively simple geometric configuration (oval as opposed to circular).

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

The invention claimed is:

1. A treatment method, comprising:
adhering a dressing with a pre-determined strain to a skin treatment location before ablating a pattern of dressing openings in the dressing or ablating a pattern of dermal tissue openings at the skin treatment location using a laser system;
ablating a pattern of dressing openings in the dressing using the laser system and ablating a pattern of dermal tissue openings at the skin treatment location using the laser system while the dressing is adhered to the skin treatment location, wherein each dermal tissue opening of the pattern of dermal tissue openings is a double-tapered tissue opening and the laser system used to form the pattern of dressing openings is the same as the laser system used to form the pattern of dermal tissue openings;
compressing the pattern of dermal tissue openings by releasing the pre-determined strain in the dressing, wherein compressing the pattern of dermal tissue openings occurs in a transverse direction to a length of each double-tapered tissue opening.

2. The treatment method of claim 1, wherein the dressing further comprises a frame.

3. The treatment method of claim 2, wherein the frame maintains the pre-determined strain of the dressing.

4. The treatment method of claim 3, further comprising aligning the laser system to indicia on the dressing.

5. The treatment method of claim 1, wherein each of the dermal tissue openings of the pattern of dermal tissue openings is a slit opening.

6. The treatment method of claim 5, wherein compressing the pattern of dermal tissue openings occurs in a transverse direction to the slit opening.

7. The treatment method of claim 1, wherein compressing the pattern of dermal tissue openings causes size reductions of the pattern of dermal tissue openings.

8. The treatment method of claim 1, wherein ablating the pattern of dressing openings occurs before ablating the pattern of dermal tissue openings.

9. The treatment method of claim 1, wherein the pre-determined strain is a unidirectional strain.

10. The treatment method of claim 1, wherein the pre-determined strain is a multi-directional strain.

11. The treatment method of claim 1, wherein the laser system comprises an Er:YAG laser.

12. The treatment method of claim 1, wherein the laser system comprises a CO2 laser.

* * * * *